US011365393B2

(12) United States Patent
Moretta et al.

(10) Patent No.: US 11,365,393 B2
(45) Date of Patent: *Jun. 21, 2022

(54) COMPOSITIONS AND METHODS FOR REGULATING NK CELL ACTIVITY

(71) Applicant: INNATE PHARMA, Marseilles (FR)

(72) Inventors: Alessandro Moretta, Genoa (IT); Mariella Della Chiesa, Santa Margherita Ligure (IT)

(73) Assignee: INNATE PHARMA, Marseilles (FR)

( * ) Notice: Subject to any disclaimer, the term of this patent is extended or adjusted under 35 U.S.C. 154(b) by 894 days.

This patent is subject to a terminal disclaimer.

(21) Appl. No.: 15/876,839

(22) Filed: Jan. 22, 2018

(65) Prior Publication Data

US 2018/0216069 A1    Aug. 2, 2018

Related U.S. Application Data

(62) Division of application No. 10/563,045, filed as application No. PCT/IB2004/002464 on Jul. 1, 2004, now Pat. No. 9,902,936.

(60) Provisional application No. 60/483,894, filed on Jul. 2, 2003, provisional application No. 60/545,471, filed on Feb. 19, 2004.

(51) Int. Cl.
| | |
|---|---|
| *A61K 39/00* | (2006.01) |
| *C12N 5/0783* | (2010.01) |
| *C07K 16/28* | (2006.01) |
| *G01N 33/569* | (2006.01) |
| *A61K 9/127* | (2006.01) |

(52) U.S. Cl.
CPC ............ *C12N 5/0646* (2013.01); *A61K 39/00* (2013.01); *C07K 16/2803* (2013.01); *G01N 33/56972* (2013.01); *A61K 9/127* (2013.01); *C07K 2317/21* (2013.01); *C07K 2317/76* (2013.01); *C07K 2317/92* (2013.01); *C07K 2319/30* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,539,094 A | 7/1996 | Reed et al. | |
| 5,583,034 A | 12/1996 | Green et al. | |
| 5,585,089 A * | 12/1996 | Queen ................ | A61P 25/00 424/133.1 |
| 5,650,491 A | 7/1997 | Reed et al. | |
| 5,660,827 A | 8/1997 | Thorpe et al. | |
| 5,808,028 A | 9/1998 | Long et al. | |
| 6,524,583 B1 | 2/2003 | Thorpe et al. | |
| 7,803,376 B2 * | 9/2010 | Velardi ................ | A61P 29/00 424/144.1 |
| 8,119,775 B2 | 2/2012 | Moretta et al. | |
| 8,551,483 B2 * | 10/2013 | Wagtmann ............ | C07K 16/08 424/144.1 |
| 8,981,065 B2 | 3/2015 | Moretta et al. | |
| 9,067,997 B2 * | 6/2015 | Romagne ............... | A61P 37/02 |
| 9,090,876 B2 * | 7/2015 | Velardi ................... | A61P 35/00 |
| 9,333,255 B2 * | 5/2016 | Wagtmann ............. | A61P 31/00 |
| 9,789,182 B2 * | 10/2017 | Graziano ........... | A61K 39/3955 |
| 9,884,593 B2 * | 2/2018 | Hull ................... | A47B 96/1475 |
| 10,059,765 B2 * | 8/2018 | Velardi .................. | A61P 35/00 |
| 10,253,095 B2 * | 4/2019 | Romagne ............... | A61P 31/14 |
| 10,494,433 B2 * | 12/2019 | Andre ................ | A61K 39/3955 |
| 10,688,180 B2 * | 6/2020 | Graziano ........... | C07K 16/2818 |
| 2002/0061581 A1 | 5/2002 | Lee et al. | |
| 2005/0037002 A1 * | 2/2005 | Velardi ................... | A61P 37/00 424/143.1 |
| 2008/0274047 A1 | 11/2008 | Romagne et al. | |
| 2008/0305117 A1 | 12/2008 | Padkaer et al. | |
| 2009/0075340 A1 | 3/2009 | Padkaer et al. | |
| 2009/0196850 A1 | 8/2009 | Romagne et al. | |
| 2009/0208416 A1 | 8/2009 | Moretta et al. | |

FOREIGN PATENT DOCUMENTS

| | | |
|---|---|---|
| EP | 0 799 836 | 10/1997 |
| WO | WO 98/16551 | 4/1998 |
| WO | WO 00/26671 | 5/2000 |
| WO | WO 2006/003179 | 1/2006 |
| WO | WO 2006/072624 | 7/2006 |
| WO | WO 2008/084106 | 7/2008 |

OTHER PUBLICATIONS

Bird et al (Science, 1988, 242: 423-426) (Year: 1988).*
Edwards et al (JMB, 2003, 334: 103-118) (Year: 2003).*
Goel et al (J. Immunol., 2004, 173: 7358-7367) (Year: 2004).*
Uehara et al (J. immunol. 2005, 175: 3424-3430) (Year: 2005).*
Perricone et al (Autoimmun. Rev. 2008, 7: 384-390) (Year: 2008).*
Torres and Casadevall (Trend. Immunol., 2008, 29(2): 91-97) (Year: 2008).*
Lloyd et al (Protein Engineering, Eng. Design & Selection, 2009, 22(3): 159-168) (Year: 2009).*
Fogel et al (Arthr. Res, Ther. 2013, 15:216, pp. 1-9) (Year: 2013).*
Selathurai et al (Cardiov. Res. 2014, 102: 128-137) (Year: 2014).*
Khan and Salunke (J. Immunol, 2014, 192: 5398-5405) (Year: 2014).*

(Continued)

*Primary Examiner* — G. R. Ewoldt
*Assistant Examiner* — Marianne DiBrino
(74) *Attorney, Agent, or Firm* — Robin L. Teskin; Baker, Donelson, Bearman, Caldwell & Berkowitz PC

(57) ABSTRACT

The present invention relates to novel compositions and methods for regulating an immune response in a subject. More particularly, the invention relates to specific antibodies that regulate the activity of NK cells and allow a potentiation of NK call cytotoxicity in mammalian subjects. The invention also relates to fragments and derivatives of such antibodies, as well as pharmaceutical compositions comprising the same and their uses, particularly in therapy, to increase NK cell activity or cytotoxicity in subjects.

20 Claims, 13 Drawing Sheets

Specification includes a Sequence Listing.

(56) References Cited

OTHER PUBLICATIONS

Poosarla et al (Biotechn. Bioeng., 2017, 114(6): 1331-1342) (Year: 2017).*
Poli et al (Trends in Immunol. 2018, 39(6): 460-472) (Year: 2018).*
AbD Serotec Datasheet: MCA2243XZ. world wide web at.abdserotec.com/catalog/datasheet-MCA2243XZ.html, May 24, 2011. 3 pages.
"Author Guide," http://bloodjournal.hematologylibrary.org/site/authors/authorgide.xhtml from Blood, 2011, 29 pages.
Barten, R. et al. "Divergent and convergent evolution of NK-cell receptors", TRENDS in Immunology, Jan. 2001, pp. 52-57, vol. 22, No. 1.
Biassoni, R. et al. "Human CD3.sup.-CD16.sup.+ Naural Killer Cells Express the hGATA-3 T Cell Transcription Factor and an Unrearranged 2 3-kb TcR σ Transcript", Eur. J Immunol., 1993, pp. 1083-1087, vol. 23.
Boyington, J. C. et al. "Crystal Structure of an NK Cell Immunoglobulin-like Receptor in Complex with its Class I MHC Ligand", Nature, Jun. 1, 2000, pp. 537-543, vol. 405.
Ciccone, E. et al. "Self class I molecules protect normal cells from lysis mediated by autologous natural killer cells" Eur. J. Immunol., 1994, pp. 1003-1006, vol. 24.
Colonna, M. et al. "Cloning of The Immunoglobulin-Superfamily Members Associated With HLA-C and HLA-B Recognition by Human Natural Killer Cells", Science, Apr. 21, 1995, pp. 405-408, vol. 268.
Database Geneseq Online Accession No. AAE17798, *E. coli* Monoclonal Antibody Heavy Chain Variable Region CDR#2, May 7, 2002, XP-002309301.
Database Geneseq Online Accession No. AAW01153, MAb 10.1 Light Chain CDR (MAb Binds Type II Phospholipase A2), Feb. 10, 1997, XP-002309300.
Database Geneseq Online Accession No. ABG74248, "Mouse Antibody 3E11 Light Chain Variable Region", Apr. 22, 2003, XP-002309299.
Eisenthal A, et al. "Induction of antibody-dependent cellular cytotoxicity in vivo by IFN-alpha and its antitumor efficacy against established B16 melanoma liver metastases when combined with specific anti-B16 monoclonal antibody," J Immunol. Jun. 1, 1990;144(11):4463-71.
Fan, Q. R. et al., :Crystal Structure of the Human Natural Killer Cell Inhibitory Receptor KIR2DL1-HLA-Cw4 Complex, Nature Immunology, May 2001, pp. 452-460, vol. 2, No. 5.
Farag, S. S. et al., "Natural Killer Cell Receptors: New Biology and Insights into the Graft-Versus-Leukemia Effect", BLOOD, Sep. 15, 2002, pp. 1935-1947, vol. 100, No. 6.
Gauthier, L et al., "μ-Surrogate Light Chain Physicochemical Interactions of the Human PreB Cell Receptor: Implications for V.sub.H Repertoire Selection and Cell Signaling at the PreB Cell Stage", The Journal of Immunology, 1999, pp. 41-50, vol. 162.
Harlow and Lane. Antibodies, A Laboratory Manual. 1988, Cold Spring Harbor Laboratory, USA, p. 287.
U.S. Appl. No. 60/489,489, Velardi, et al.
Karre, K. et al. "Selective Rejection of H-2-Deficient Lymphoma Variants Suggests Alternative Immune Defence Strategy", Nature, Feb. 20, 1986, pp. 675-678, vol. 319.
Kim J, et al. "Molecular basis of HLA-C recognition by p58 natural killer cell inhibitory receptors," J Immunol. Oct. 15, 1997;159(8):3875-82.
Koh, C. Y. et al. "NK Inhibitory-Receptor Blockade for Purging of Leukemia: Effects on Hematopoietic Reconstitution", Biology of Blood and Marrow Transplantation, 2002, pp. 17-25, vol. 8.
Lanier, L. "Nk Cell Receptors", Annu. Rev. Immunol., 198, pp. 359-393 vol. 16.
Maenaka, K. et al. "Crystal Structure of the Human p58 Killer Cell Inhibitory Receptor (KIR2DL3) Specific for HLA-Cw3-Related MHC Class I", Structure, Apr. 1999, pp. 391-398, vol. 7, No. 4.
Moretta, A. et al. "Activating Receptors and Coreceptors Involved Human Natural Killer Cell-Mediated Cytolysis", Annu. Rev. Immunol., 2001, pp. 197-223 and Table of Contents, vol. 19.
Moretta, A. et al. "Identification of Four Subsets of Human CD3.sup.-CD16.sup.+ Natural Killer (NK) Cells by the Expression of Clonally Distributed Functional Surface Molecules: Correlation between Subset Assignment of NK Clones and Ability to Mediate Specific Alloantigen Recognition", J. Exp. Med., Dec. 1990, pp. 1589-1598, vol. 172.
Morettta, A. et al. "A Novel Surface Antigen Expressed by a Subset of Human CD3.sup.-CD16.sup.+ Natural Killer Cells", The Journal of Experimental Medicine, Mar. 1990 , pp. 695-714. vol. 171.
Moretta, A et al. "P58 Molecules as Putative Receptors for Major Histocompatibility Complex (MHC) Class I Molecules in Human Natural Killer (NK) Cells. Anti-p58 Antibodies Reconstitute Lysis of MHC Class I-protected Cells in NK Clones Displaying Different Specificitites", J. Exp. Med., Aug. 1993, pp. 597-604, vol. 178.
Moretta, A. et al. "Receptors for HLA Class-I Molecules in Human Natural Killer Cells", Annu. Rev. Immunol., 1996, pp. 619-648, vol. 14.
Moretta, A. et al. "Function And Specificity of Human Natural Killer Cell Receptors", Eur. J. Immunogenetics, 1997, pp. 455-468, vol. 24.
Natarajan K., et al. "Structure and function of natural killer cell receptors: multiple molecular solutions to self, nonself discrimination," Annu Rev Immunol 2002;20:853-85. Epub Oct. 4, 2001.
Ohlen, C. et al. "Studies of Sublines Selected for Loss of HLA Expression From An Ebv-Transformed Lymphoblastoid Cell Line. Changes in Sensitivity to Cytotoxic T Cells Activated by Allostimulation and Natural Killer Cells Activated by IFN or IL-2", J Immunol., May 1, 1989, pp. 3336-3341, vol. 142, No. 9.
Pende, D. et al. "Identification and Molecular Characterization of NKp30, a Novel Triggering Receptor Involved in Natural Cytotoxicity Mediated by Human Natural Killer Cells", J. Exp. Med., Nov. 15, 1999, pp. 1505-1516, vol. 190, No. 10.
Poggi, A. et al. "P40, A Novel Surface Molecule Involved in the Regulation of the Non-Major Histocompatibility Complex—Restricted Cytolytic activity in Humans", European Journal of Immunology, 1995, pp. 369-376, vol. 25.
Ruggeri, L. et al. "Effectiveness of Donor Natural Killer Cell Alloreactivity in Mismatched Hematopoietic Transplants", Science, Mar. 15, 2002, pp. 2097-2100, vol. 295.
Saunal, H. et al. "Mapping of Viral Conformational Epitopes Using Biosensor Measurements", Journal of Immunological Methods, 1995, pp. 33-41, vol. 183.
Saulquin, X. et al. "Crystal Structure of the Human Natural Killer Cell Activating Receptor KIR2DS2 (CD158j)", J. Exp. Med., Apr. 7, 2003, pp. 933-938, vol. 197, No. 7.
Sears, D.W., "Complex Betweeen HEL Antigen and Anti-HEL Antibody Fab," (2009, mcdb-webarchive.mcdb.ucsb.edu/sears.immunology/Antibody-Antigen). 2 pages.
Shin, J.-S. et al. "Monoclonal Antibodies with Various Reactivity to p58 Killer Inhibitory Receptors", Hybridoma, 1999, pp. 521-527, vol. 18, No. 6.
Sims MJ, et al. "A humanized CD18 antibody can block function without cell destruction,".
Smyth MJ, et al. "New aspects of natural-killer-cell surveillance and therapy of cancer," Nat Rev Cancer. Nov. 2002;2 (11):850-61.
Spaggiari, G. M. et al. "Soluble HLA Class I Induces NK Cell Apoptosis Upon the Engagement of Killer-Activating HLA Class I Receptors through FasL-Fas Interaction", Blood, Dec. 1, 2002, pp. 4098-4107, vol. 100, No. 12.
Spaggiari, G. M. et al. "Soluble HLA class I Molecules Induce Natural Killer Cell Apoptosis Through The Engagement of CD8: Evidence for A Negative Regulation Exerted by Members of the Inhibitory Receptor Superfamily", Blood, Mar. 1, 2002, pp. 1706-1714, vol. 99, No. 5.
Sun et al., "Chimeric antibody with human constant regions and mouse variable regions directed against carcinoma-associated antigen 17-1A," Proc. Natl. Acad Sci. USA, Jan. 1987, pp. 214-218, vol. 84.
Valiante, N. et al. "Killer Cell Receptors: Keeping Pace With MHC Class I Evolution", Immunol. Rev., 1997, pp. 155-164, vol. 155.
Vitale, M. et al. "Coexpression of two functionally independent p58 inhibitory receptors in human natural killer cell clones results in the

(56) References Cited

OTHER PUBLICATIONS inability to kill all normal allogeneic target cells" Proc. Natl. Acad. Sci. USA, Apr. 1995, pp. 3536-3540, vol. 92.

Wagtmann, N. et al. "Killer Cell Inhibitory Receptors Specific for HLA-C and HLA-B ildentified by Direct Binding and by Functional Transfer", Immunity, Dec. 1995, pp. 801-809, vol. 3.

Wagtmann, N. et al. "Molecular Clones of the p58 NK Cell Receptor Reveal Immunoglobulin-Related Molecules with Diversity in Both the Extra- and Intracellular Domains", Immunity, May 1995, pp. 439-449, vol. 2.

Warren, H.S. et al. "Functional analysis of CD158b monoclonal antibodies recognizing the killer Ig-like receptors KIR2DS2, KIR2DL2 and KIR2DL3", Tissue Antigens, 2000, pp. 80-81, vol. 55, No. Supplement 15, XP009040899 (abstract only).

Watzl, C. et al. "Homogenous Expression of Killer Cell Immunoglobulin-Like Receptors (KIR) on Polyclonal Natural Killer Cells Detected by A Monoclonal Antibody to KIR2D", Tissue Antigens, 2000, pp. 240-247, vol. 56.

Winter CC, et al. "A single amino acid in the p58 killer cell inhibitory receptor controls the ability of natural killer cells to discriminate between the two groups of HLA-C allotypes," J Immunol. May 1, 1997;158(9):4026-8.

Pending claims for U.S. Appl. No. 11/630,176, filed Dec. 19, 2006.
Pending claims for U.S. Appl. No. 11/813,399, filed May 21, 2008.
Pending claims for U.S. Appl. No. 12/521,105, filed Jun. 24, 2009.

\* cited by examiner

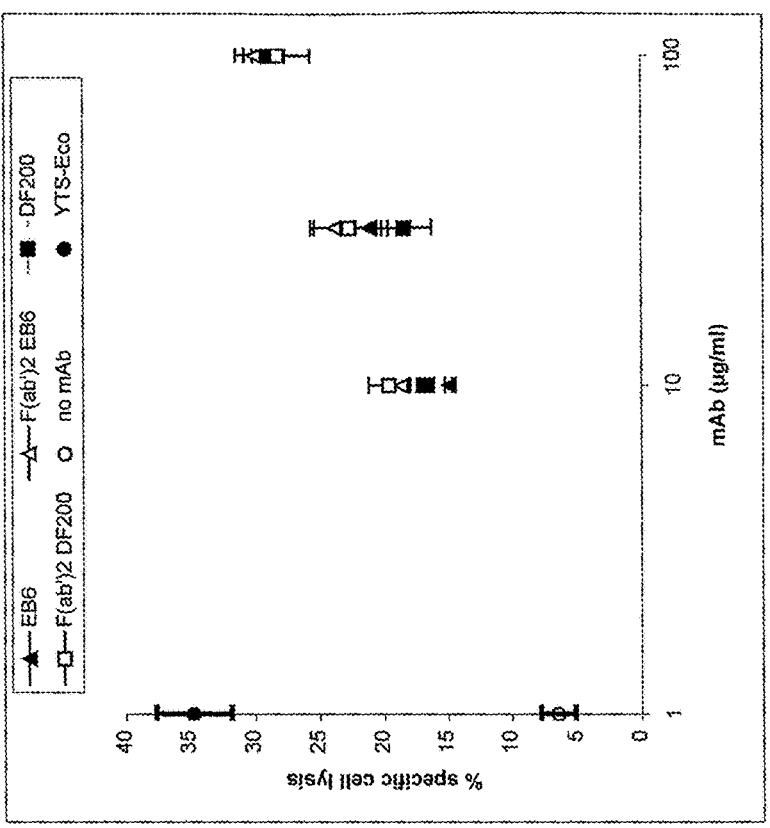
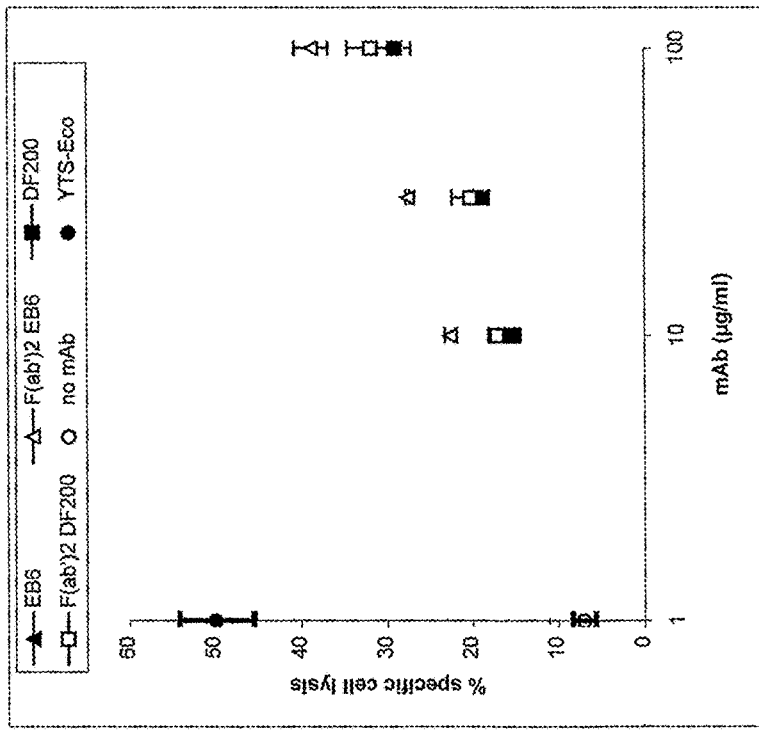

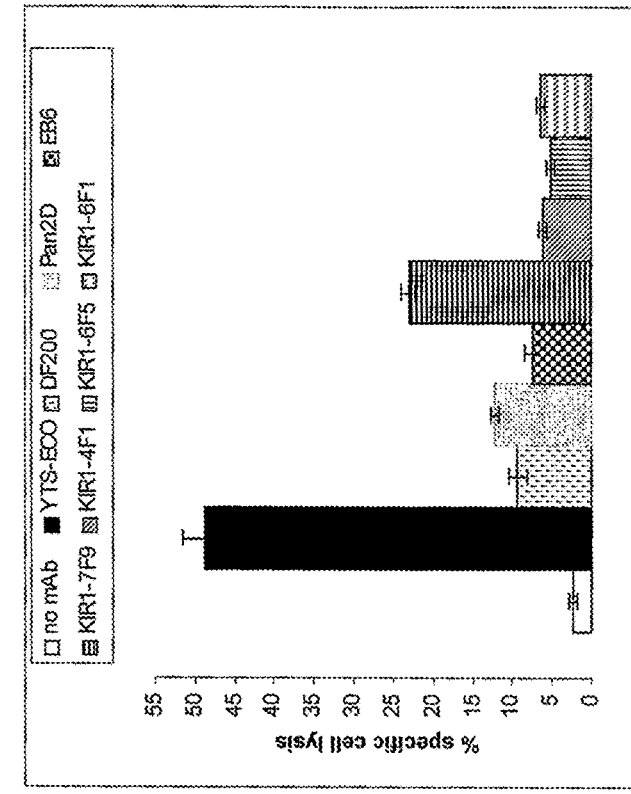
FIG 5A : mAb: 30μg/ml
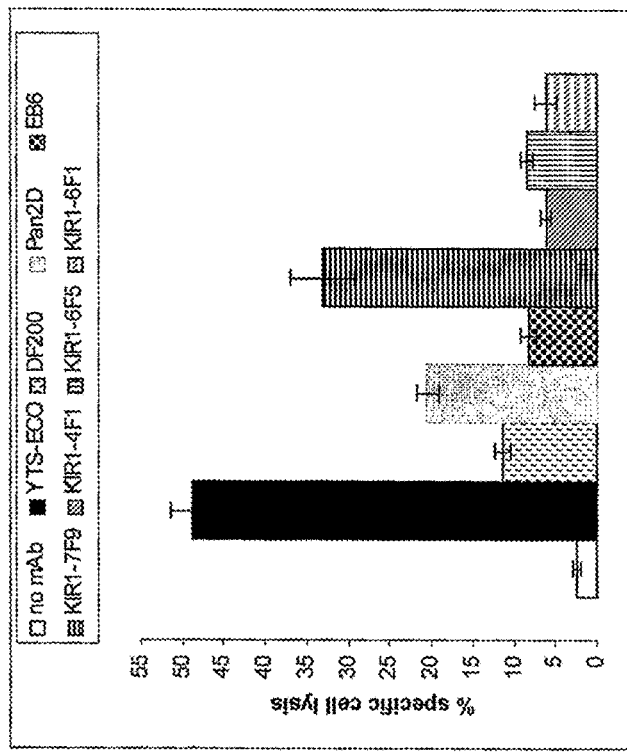
FIG 5B : mAb: 10μg/ml
E/T ratio= 1

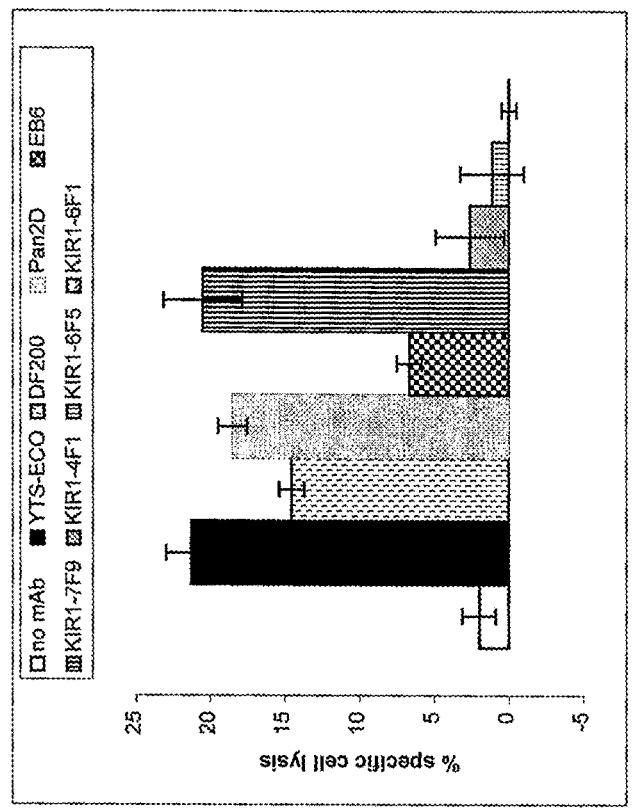
FIG 6A: mAb: 30μg/ml
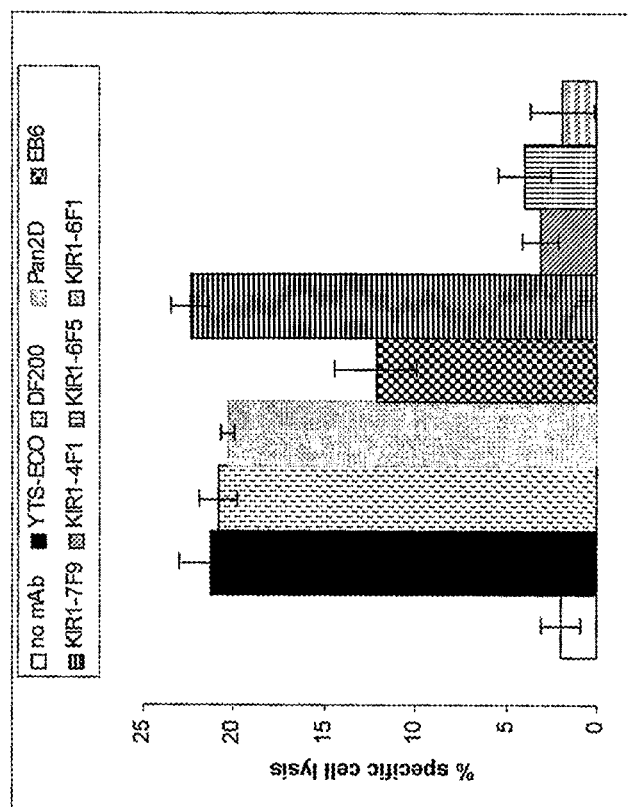
FIG 6B: mAb: 10μg/ml
E/T ratio= 2

FIG 11A KIR2DL1(R131W)-hFc
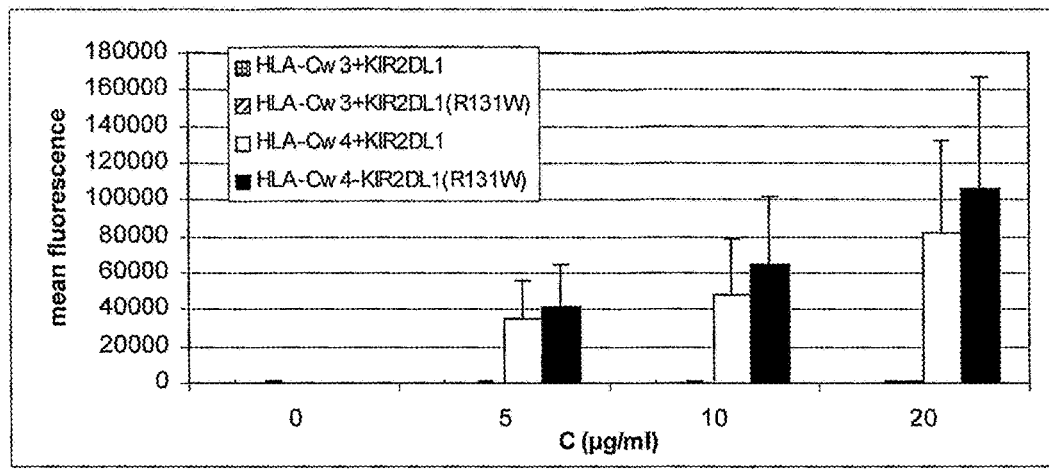
FIG 11B
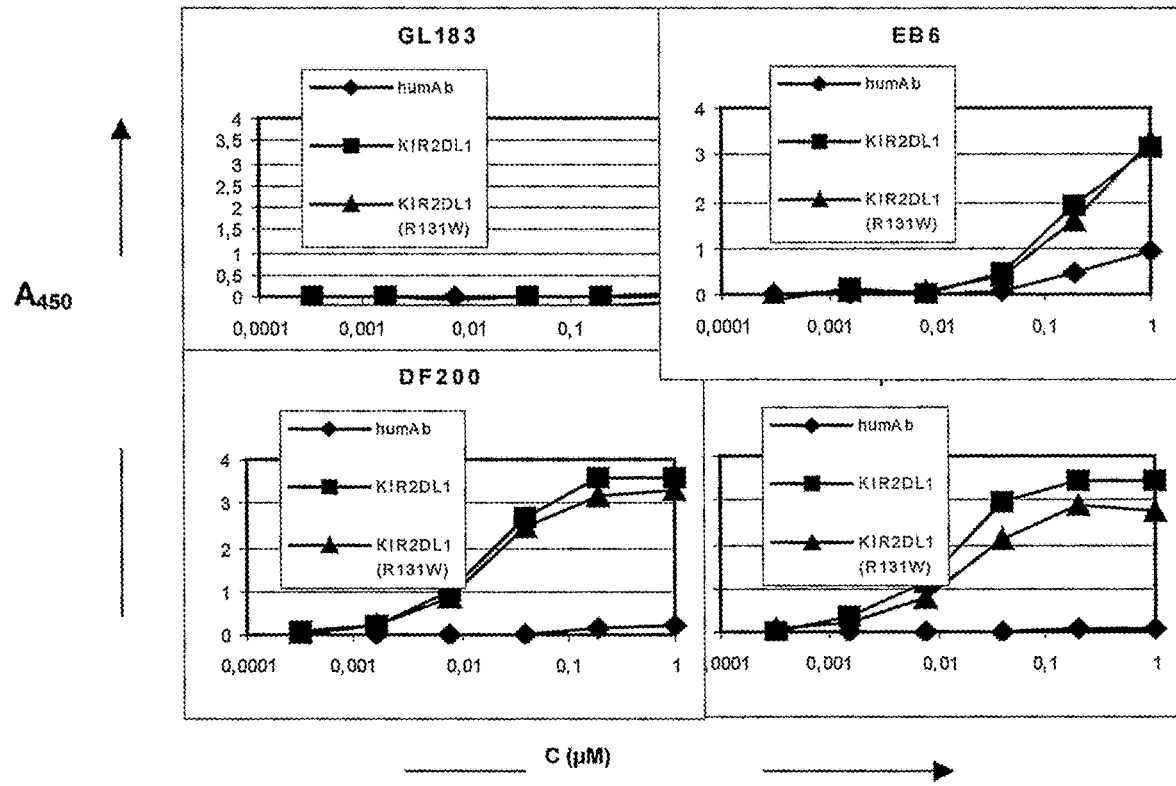

FIG 12

Anti-KIR light variable regions

```
                        1                                                50
DF-200 light variable  (1) M--ESQTLVFISILLWLYGADGNIVMTQSPKSMSMSVGERVTLTCKASEN
PAN2D-Light-variable   (1) MDFQVQIFSFLLISASVIMSRGQIVLTQSPASMSASLGERVTMTCTASSS
          Consensus    (1)          Q   FI I  L A GNIVLTQSP SMS SLGERVTLTC AS 51                                               100
DF-200 light variable (49) VVT-INSWYQQKPEQSPKLLIYGASNRYTGVPDRFTGSGSATDFLTISS
PAN2D-Light-variable  (51) VSSSYLYWYQQKPGSSPKLWIYSTSNLASGVPARFSGSGSGTSYSLTISS
          Consensus   (51) V S YL WYQQKP SPKL IY  SN  SGVP RFSGSGSAT FSLTISS 101                     131
DF-200 light variable (98) VQAEDLADYHCGQGYSYPYTFGGGTKLEIKR  (SEQ ID NO:1)
PAN2D-Light-variable (101) MEAEDAATYHCHQYHRSPPTFGGGTKLEIKR  (SEQ ID NO:2)
          Consensus  (101) M AED A YHC Q H  P TFGGGTKLEIKR  (SEQ ID NO:13)
```

Numbers above amino acid sequences indicate position respective to initiation of translation Met (+1) in the immature (non-secreted) immunoglobulin. Underlined are the CDR regions

CDR's from the anti-KIR light variable regions

| CDR-L1 from clones PAN-2D and DF-200 |
|---|
| Residue before: Normally Cys. Residues after: Trp. Typically Trp-Tyr-Leu.Length: 10-17 aa |
| Start: approximately 24 aa from the beginning of secreted protein |
| DF-200 light variable (44) KASENVLT-YVS (SEQ ID NO:3) |
| PAN2D-Light-variable (46) TASSSVSSSYLY (SEQ ID NO:4) |
| Consensus                AS V S YL    (SEQ ID NO:14) |

| CDR-L2 from clones PAN-2D and DF-200 |
|---|
| Residues before: Generally Ile-Tyr |
| Length: 7 aa |
| Start: approximately 16 aa after the end of CDR-L1 |
| DF-200 light variable (70) GASNRYT (SEQ ID NO:5) |
| PAN2D-Light-variable (73) STSNLAS (SEQ ID NO:6) |
| Consensus                SN   S  (SEQ ID NO:15) |

| CDR-L3 from clones PAN-2D and DF-200 |
|---|
| Residues before: Cys |
| Residues after: Phe-Gly-XXX-Gly |
| Length: 7-11 aa |
| Start: approximately 33 aa after the end of CDR-L2 |
| DF-200 light variable (109) GQGYSYPYT (SEQ ID NO:7) |
| PAN2D-Light-variable (112) HQYHRSPPT (SEQ ID NO:8) |
| Consensus                   Q H  P T (SEQ ID NO:16) |

FIG 13

>DF-200\VH\immature-PROT
MAVLGLLFCLVTFPSCVLS
QVQLEQSGPGLVQPSQSLSITCTVSGFSFTPYGVHWVRQSPGKGLEWLGVIWSGGNTDYNAAFISRLSINKDNSKSQVFFK
MNSLQVNDTAIYYCARNPRPGNYPYGMDYWGQGTSVTVSS (SEQ ID NO: 9)

Anti-KIR heavy variable regions (immature Fabs)

Sequences including CDR regions in heavy variable regions

| CDR-H1 from clone DF-200 | CDR-H2 from clone DF-200 |
|---|---|
| Residues before: Cys-XXX-XXX-XXX<br>Residues after: Trp. Generally Trp-Val or Trp-Ile<br>Length: 10-14 aa<br>Start: Approximately 22-26 aa from the beginning of the secreted protein<br><br>GFSFTPYGVH (SEQ ID NO: 10) | Residues before: Leu-Glu-Trp-Ile-Gly but other variations possible<br>Residues after: Lys or Arg / Leu or Ile or Val or Phe or Thr or Ala / Thr or Ser or Ile or Ala<br>Length: 16-20 aa<br>Start: Approximately 15 aa after the end of CDR-H1<br><br>VIWSGGNTDYNAAFIS (SEQ ID NO: 11) |
| CDR-H3 from clones 4G1, 5D5 and 6C12<br>Residues before: Cys-XXX-XXX (Typically Cys-Ala-Arg)<br>Residues after: Trp-Gly-XXX-Gly<br>Length: 3-25 aa<br>Start: Approximately 33 after the end of CDR-H2<br><br>NPRPGNYPYGMDY (SEQ ID NO: 12) | |

The secreted, mature VH starts at:
Position 20: residue Q

The VH region ends with residue S and thereafter the constant region (not shown) continues

SEQUENCE LISTING

```
<160> NUMBER OF SEQ ID NOS: 18

<210> SEQ ID NO 1
<211> LENGTH: 128
<212> TYPE: PRT
<213> ORGANISM: Mus musculus

<400> SEQUENCE: 1

Met Glu Ser Gln Thr Leu Val Phe Ile Ser Ile Leu Leu Trp Leu Tyr
1               5                   10                  15
```

Gly Ala Asp Gly Asn Ile Val Met Thr Gln Ser Pro Lys Ser Met Ser
            20                  25                  30

Met Ser Val Gly Glu Arg Val Thr Leu Thr Cys Lys Ala Ser Glu Asn
        35                  40                  45

Val Val Thr Tyr Val Ser Trp Tyr Gln Gln Lys Pro Glu Gln Ser Pro
    50                  55                  60

Lys Leu Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Gln Ala Glu Asp Leu Ala Asp Tyr His Cys Gly Gln Gly Tyr
            100                 105                 110

Ser Tyr Pro Tyr Thr Phe Gly Gly Gly Thr Lys Leu Glu Ile Lys Arg
        115                 120                 125

<210> SEQ ID NO 2
<211> LENGTH: 131
<212> TYPE: PRT
<213> ORGANISM: Mus musculus

<400> SEQUENCE: 2

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ser
            20                  25                  30

Met Ser Ala Ser Leu Gly Glu Arg Val Thr Met Thr Cys Thr Ala Ser
        35                  40                  45

Ser Ser Val Ser Ser Ser Tyr Leu Tyr Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Ser Pro Pro Thr Phe Gly Gly Gly Thr Lys Leu Glu
        115                 120                 125

Ile Lys Arg
    130

<210> SEQ ID NO 3
<211> LENGTH: 11
<212> TYPE: PRT
<213> ORGANISM: Mus musculus

<400> SEQUENCE: 3

Lys Ala Ser Glu Asn Val Val Thr Tyr Val Ser
1               5                   10

<210> SEQ ID NO 4
<211> LENGTH: 12
<212> TYPE: PRT
<213> ORGANISM: Mus musculus

<400> SEQUENCE: 4

Thr Ala Ser Ser Ser Val Ser Ser Ser Tyr Leu Tyr
1               5                   10

```
<210> SEQ ID NO 5
<211> LENGTH: 7
<212> TYPE: PRT
<213> ORGANISM: Mus musculus

<400> SEQUENCE: 5

Gly Ala Ser Asn Arg Tyr Thr
1               5

<210> SEQ ID NO 6
<211> LENGTH: 7
<212> TYPE: PRT
<213> ORGANISM: Mus musculus

<400> SEQUENCE: 6

Ser Thr Ser Asn Leu Ala Ser
1               5

<210> SEQ ID NO 7
<211> LENGTH: 9
<212> TYPE: PRT
<213> ORGANISM: Mus musculus

<400> SEQUENCE: 7

Gly Gln Gly Tyr Ser Tyr Pro Tyr Thr
1               5

<210> SEQ ID NO 8
<211> LENGTH: 9
<212> TYPE: PRT
<213> ORGANISM: Mus musculus

<400> SEQUENCE: 8

His Gln Tyr His Arg Ser Pro Pro Thr
1               5

<210> SEQ ID NO 9
<211> LENGTH: 140
<212> TYPE: PRT
<213> ORGANISM: Mus musculus

<400> SEQUENCE: 9

Met Ala Val Leu Gly Leu Leu Phe Cys Leu Val Thr Phe Pro Ser Cys
1               5                   10                  15

Val Leu Ser Gln Val Gln Leu Glu Gln Ser Gly Pro Gly Leu Val Gln
                20                  25                  30

Pro Ser Gln Ser Leu Ser Ile Thr Cys Thr Val Ser Gly Phe Ser Phe
            35                  40                  45

Thr Pro Tyr Gly Val His Trp Val Arg Gln Ser Pro Gly Lys Gly Leu
    50                  55                  60

Glu Trp Leu Gly Val Ile Trp Ser Gly Gly Asn Thr Asp Tyr Asn Ala
65                  70                  75                  80

Ala Phe Ile Ser Arg Leu Ser Ile Asn Lys Asp Asn Ser Lys Ser Gln
                85                  90                  95

Val Phe Phe Lys Met Asn Ser Leu Gln Val Asn Asp Thr Ala Ile Tyr
                100                 105                 110

Tyr Cys Ala Arg Asn Pro Arg Pro Gly Asn Tyr Pro Tyr Gly Met Asp
            115                 120                 125

Tyr Trp Gly Gln Gly Thr Ser Val Thr Val Ser Ser
    130                 135                 140
```

```
<210> SEQ ID NO 10
<211> LENGTH: 10
<212> TYPE: PRT
<213> ORGANISM: Mus musculus

<400> SEQUENCE: 10

Gly Phe Ser Phe Thr Pro Tyr Gly Val His
1               5                   10

<210> SEQ ID NO 11
<211> LENGTH: 16
<212> TYPE: PRT
<213> ORGANISM: Mus musculus

<400> SEQUENCE: 11

Val Ile Trp Ser Gly Gly Asn Thr Asp Tyr Asn Ala Ala Phe Ile Ser
1               5                   10                  15

<210> SEQ ID NO 12
<211> LENGTH: 13
<212> TYPE: PRT
<213> ORGANISM: Mus musculus

<400> SEQUENCE: 12

Asn Pro Arg Pro Gly Asn Tyr Pro Tyr Gly Met Asp Tyr
1               5                   10

<210> SEQ ID NO 13
<211> LENGTH: 91
<212> TYPE: PRT
<213> ORGANISM: Mus musculus

<400> SEQUENCE: 13

Gln Phe Ile Ile Leu Ala Gly Asn Ile Val Leu Thr Gln Ser Pro Ser
1               5                   10                  15

Met Ser Ser Leu Gly Glu Arg Val Thr Leu Thr Cys Ala Ser Val Ser
            20                  25                  30

Tyr Leu Trp Tyr Gln Gln Lys Pro Ser Pro Lys Leu Ile Tyr Ser Asn
        35                  40                  45

Ser Gly Val Pro Arg Phe Ser Gly Ser Gly Ser Ala Thr Phe Ser Leu
    50                  55                  60

Thr Ile Ser Ser Met Ala Glu Asp Ala Tyr His Cys Gln His Pro Thr
65                  70                  75                  80

Phe Gly Gly Gly Thr Lys Leu Glu Ile Lys Arg
                85                  90

<210> SEQ ID NO 14
<211> LENGTH: 6
<212> TYPE: PRT
<213> ORGANISM: Mus musculus

<400> SEQUENCE: 14

Ala Ser Val Ser Tyr Leu
1               5

<210> SEQ ID NO 15
<211> LENGTH: 3
<212> TYPE: PRT
<213> ORGANISM: Mus musculus

<400> SEQUENCE: 15

Ser Asn Ser
1
```

```
<210> SEQ ID NO 16
<211> LENGTH: 4
<212> TYPE: PRT
<213> ORGANISM: Mus musculus

<400> SEQUENCE: 16

Gln His Pro Thr
1

<210> SEQ ID NO 17
<211> LENGTH: 42
<212> TYPE: DNA
<213> ORGANISM: Mus musculus

<400> SEQUENCE: 17
ggaattccag gaggaattta aaatgcatga gggagtccac ag                              42

<210> SEQ ID NO 18
<211> LENGTH: 26
<212> TYPE: DNA
<213> ORGANISM: Mus musculus

<400> SEQUENCE: 18
cgggatccca ggtgtctggg gttacc                                               26
```

COMPOSITIONS AND METHODS FOR REGULATING NK CELL ACTIVITY

This application is a divisional of U.S. application Ser. No. 10/563,045, filed Jun. 30, 2006, now U.S. Pat. No. 9,902,936, which is a U.S. 371 application of international application PCT/IB04/02464 filed Jul. 1, 2004 (published as WO/2005/003172) which claims priority to U.S. Provisional Application 60/483,894 filed Jul. 2, 2003 and U.S. Provisional Application 60/545,471 filed Feb. 19, 2004, the disclosure of all of which listed above are herein incorporated by reference in their entirety.

FIELD OF INVENTION

The present invention relates to antibodies, antibody fragments, and derivatives thereof that cross-react with two or more inhibitory receptors present on the cell surface of NK cells and potentiate NK cell cytotoxicity in mammalian subjects or in a biological sample. The invention also relates to methods of making such antibodies, fragments, variants, and derivatives; pharmaceutical compositions comprising the same; and the use of such molecules and compositions, particularly in therapy, to increase NK cell activity or cytotoxicity in subjects.

SEQUENCE LISTING DISCLOSURE

This application includes as part of its disclosure a biological sequence listing contained in a file named "43271o1802.txt" having a size of 6,096 bytes that was created Jan. 22, 2018, which is hereby incorporated by reference in its entirety.

BACKGROUND

Natural killer (NK) cells are a sub-population of lymphocytes, involved in non-conventional immunity. NK cells can be obtained by various techniques known in the art, such as from blood samples, cytapheresis, collections, etc.

Characteristics and biological properties of NK cells include the expression of surface antigens including CD16, CD56, and/or CD57; the absence of the alpha/beta or gamma/delta TCR complex on the cell surface; the ability to bind to and kill cells that fail to express "self" MHC/HLA antigens by the activation of specific cytolytic enzymes; the ability to kill tumor cells or other diseased cells that express a NK activating receptor-ligand; the ability to release cytokines that stimulate or inhibit the immune response; and the ability to undergo multiple rounds of cell division and produce daughter cells with similar biologic properties as the parent cell. Within the context of this invention "active" NK cells designate biologically active NK cells, more particularly NK cells having the capacity of lysing target cells. For instance, an "active" NK cell is able to kill cells that express an NK activating receptor-ligand and fail to express "self" MHC/HLA antigens (KIR-incompatible cells).

Based on their biological properties, various therapeutic and vaccine strategies have been proposed in the art that rely on a modulation of NK cells. However, NK cell activity is regulated by a complex mechanism that involves both stimulating and inhibitory signals. Accordingly, effective NK cell-mediated therapy may require both a stimulation of these cells and a neutralization of inhibitory signals.

NK cells are negatively regulated by major histocompatibility complex (MHC) class I-specific inhibitory receptors (Kärre et al., 1986; Öhlén et al, 1989). These specific receptors bind to polymorphic determinants of MHC class I molecules or HLA present on other cells and inhibit NK cell lysis. In humans, certain members of a family of receptors termed killer Ig-like receptors (KIRs) recognize groups of HLA class I alleles.

KIRs are a large family of receptors present on certain subsets of lymphocytes, including NK cells. The nomenclature for KIRs is based upon the number of extracellular domains (KIR2D or KIR3D) and whether the cytoplasmic tail is either long (KIR2DL or KIR3DL) or short (KIR2DS or KIR3DS). Within humans, the presence or absence of a given KIR is variable from one NK cell to another within the NK population present in a single individual. Within the human population there is also a relatively high level of polymorphism of the KIR molecules, with certain KIR molecules being present in some, but not all individuals. Certain KIR gene products cause stimulation of lymphocyte activity when bound to an appropriate ligand. The confirmed stimulatory KIRs all have a short cytoplasmic tail with a charged transmembrane residue that associates with an adapter molecule having an immunostimulatory motif (ITAM). Other KIR gene products are inhibitory in nature. All confirmed inhibitory KIRs have a long cytoplasmic tail and appear to interact with different subsets of HLA antigens depending upon the KIR subtype. Inhibitory KIRs display in their intracytoplasmic portion one or several inhibitory motifs that recruit phosphatases. The known inhibitory KIR receptors include members of the KIR2DL and KIR3DL subfamilies. KIR receptors having two Ig domains (KIR2D) identify HLA-C allotypes: KIR2DL2 (formerly designated p58.2) or the closely related gene product KIR2DL3 recognizes an epitope shared by group 2 HLA-C allotypes (Cw1, 3, 7, and 8), whereas KIR2DL1 (p58.1) recognizes an epitope shared by the reciprocal group 1 HLA-C allotypes (Cw2, 4, 5, and 6). The recognition by KIR2DL1 is dictated by the presence of a Lys residue at position 80 of HLA-C alleles. KIR2DL2 and KIR2DL3 recognition is dictated by the presence of an Asn residue at position 80. Importantly the great majority of HLA-C alleles have either an Asn or a Lys residue at position 80. One KIR with three Ig domains, KIR3DL1 (p70), recognizes an epitope shared by HLA-Bw4 alleles. Finally, a homodimer of molecules with three Ig domains KIR3DL2 (p140) recognizes HLA-A3 and -A11.

Although inhibitory KIRs and other class-I inhibitory receptors (Moretta et al, 1997; Valiante et al, 1997a; Lanier, 1998) may be co-expressed by NK cells, in any given individual's NK repertoire there are cells that express a single KIR and thus, the corresponding NK cells are blocked only by cells expressing a specific class I allele group.

NK cell population or clones that are KIR mismatched, i.e., population of NK cells that express KIR that are not compatible with a HLA molecules of a host, have been shown to be the most likely mediators of the graft anti-leukemia effect seen in allogeneic transplantation (Ruggeri et al., 2002). One way of reproducing this effect in a given individual would be to use reagents that block the KIR/HLA interaction.

Monoclonal antibodies specific for KIR2DL1 have been shown to block the interaction of KIR2DL1 with Cw4 (or the like) alleles (Moretta et al., 1993). Monoclonal antibodies against KIR2DL2/3 have also been described that block the interaction of KIR2DL2/3 with HLACw3 (or the like) alleles (Moretta et al., 1993). However, the use of such reagents in clinical situations would require the development of two therapeutic mAbs to treat all patients, regardless of whether any given patient was expressing class 1 or class 2 HLA-C alleles. Moreover, one would have to pre-determine which HLA type each patient was expressing before deciding which therapeutic antibody to use, thus resulting in much higher cost of treatment.

Watzl et al., *Tissue Antigens*, 56, p. 240 (2000) produced cross-reacting antibodies recognizing multiple isotypes of KIRs, but those antibodies did not exhibit potentiation of NK cell activity. G. M. Spaggiara et al., *Blood*, 100, pp. 4098-4107 (2002) carried out experiments utilizing numerous monoclonal antibodies against various KIRs. One of those antibodies, NKVSF1, was said to recognize a common epitope of CD158a KIR2DL1), CD158b (KIR2DL2) and p50.3 (KIR2DS4). It is not suggested that NKVSF1 can potentiate NK cell activity and there is no suggestion that it could be used as a therapeutic. Accordingly, practical and effective approaches in the modulation of NK cell activity have not been made available so far in the art and still require HLA allele-specific intervention using specific reagents.

SUMMARY OF THE INVENTION

The present invention now provides novel antibodies, compositions, and methods that overcome current difficulties in NK cell activation and provide additional advantageous features and benefits. In one exemplary aspect, the invention provides a single antibody that facilitates the activation of human NK cells in virtually all humans. More particularly, the invention provides novel specific antibodies that cross-react with various inhibitory KIR groups and neutralize their inhibitory signals, resulting in potentiation of NK cell cytotoxicity in NK cells expressing such inhibitory KIR receptors. This ability to cross-react with multiple KIR gene products allows the antibodies of the invention to be effectively used to increase NK cell activity in most human subjects, without the burden or expense of pre-determining the HLA type of the subject.

In a first aspect, the invention provides antibodies, antibody fragments, and derivatives of either thereof, wherein said antibody, fragment, or derivative cross-reacts with at least two inhibitory KIR receptors at the surface of NK cells, neutralizes the inhibitory signals of the NK cells, and potentiates the activity of the NK cells. More preferably, the antibody binds a common determinant of human KIR2DL receptors. Even more specifically, the antibody of this invention binds at least KIR2DL1, KIR2DL2, and KIR2DL3 receptors. For the purposes of this invention, the term "KIR2DL2/3" refers to either or both of the KIR2DL2 and KIR2DL3 receptors. These two receptors have a very high homology, are presumably allelic forms of the same gene, and are considered by the art to be interchangeable. Accordingly, KIR2DL2/3 is considered to be a single inhibitory KIR molecule for the purposes of this invention and therefore an antibody that cross-reacts with only KIR2DL2 and KIR2DL3 and no other inhibitory KIR receptors is not within the scope of this invention.

The antibody of this invention specifically inhibits binding of MHC or HLA molecules to at least two inhibitory KIR receptors and facilitates NK cell activity. Both activities are inferred by the term "neutralize the inhibitory activity of KIR," as used herein. The ability of the antibodies of this invention to "facilitate NK cell activity," "facilitate NK cell cytotoxicity," "facilitate NK cells," "potentiate NK cell activity," "potentiate NK cell cytotoxicity," or "potentiate NK cells" in the context of this invention means that the antibody permits NK cells expressing an inhibitory KIR receptor on their surface to be capable of lysing cells that express on their surface a corresponding ligand for that particular inhibitory KIR receptor (e.g., a particular HLA antigen). In a particular aspect, the invention provides an antibody that specifically inhibits the binding of HLA-C molecules to KIR2DL1 and KIR2DL2/3 receptors. In another particular aspect, the invention provides an antibody that facilitates NK cell activity in vivo.

Because at least one of KIR2DL1 or KID2DL2/3 is present in at least about 90% of the human population, the more preferred antibodies of this invention are capable of facilitating NK cell activity against most of the HLA-C allotype-associated cells, respectively group 1 HLA-C allotypes and group 2 HLA-C allotypes. Thus, compositions of this invention may be used to effectively activate or potentiate NK cells in most human individuals, typically in about 90% of human individuals or more. Accordingly, a single antibody composition according to the invention may be used to treat most human subjects, and there is seldom need to determine allelic groups or to use antibody cocktails.

The invention demonstrates, for the first time, that cross-reactive and neutralizing antibodies against inhibitory KIRs may be generated, and that such antibodies allow effective activation of NK cells in a broad range of human groups.

A particular object of this invention thus resides in an antibody, wherein said antibody specifically binds both KIR2DL1 and KIR2DL2/3 human receptors and reverses inhibition of NK cell cytotoxicity mediated by these KIRs. In one embodiment, the antibody competes with monoclonal antibody DF200 produced by hybridoma DF200. Optionally said antibody which competes with antibody DF200 is not antibody DF200 itself.

In another embodiment, the antibody competes with monoclonal antibody NKVSF1, optionally wherein the antibody which competes with antibody NKVSF1 is not antibody NKVSF1.

In another embodiment, the antibody competes with antibody 1-7F9.

Preferably said antibodies are chimeric antibodies, humanized antibodies, or human antibodies.

The term "competes with" when referring to a particular monoclonal antibody (e.g. DF200, NKVSF1, 1-7F9, EB6, GL183) means that an antibody competes with the monoclonal antibody (e.g. DF200, NKVSF1, 1-7F9, EB6, GL183) in a binding assay using either recombinant KIR molecules or surface expressed KIR molecules. For example, if an antibody reduces binding of DF200 to a KIR molecule in a binding assay, the antibody "competes" with DF200. An antibody that "competes" with DF200 may compete with DF200 for binding to the KIR2DL1 human receptor, the KIR2DL2/3 human receptor, or both KIR2DL1 and KIR2DL2/3 human receptors.

In a preferred embodiment, the invention provides an antibody that binds both KIR2DL1 and KIR2DL2/3 human receptors, reverses inhibition of NK cell cytotoxicity mediated by these KIRs, and competes with DF200, 1-7F9, or NKVSF1 for binding to the KIR2DL1 human receptor, the KIR2DL2/3 human receptor, or both KIR2DL1 and KIR2DL2/3 human receptors. Optionally, said antibody is not NKVSF1. Optionally, said antibody is a chimeric, human, or humanized antibody.

In another embodiment, the invention provides an antibody that binds both KIR2DL1 and KIR2DL2/3 human receptors, reverses inhibition of NK cell cytotoxicity mediated by these KIRs, and competes with EB6 for binding to the KIR2DL1 human receptor, competes with GL183 for binding to the KIR2DL2/3 human receptor, or competes with both EB6 for binding to the KIR2DL1 human receptor and GL183 for binding to the KIR2DL2/3 human receptor.

Optionally, said antibody is not NKVSF1; optionally said antibody is not DF200. Optionally, said antibody is a chimeric, human, or humanized antibody.

In an advantageous aspect, the invention provides an antibody that competes with DF200 and recognizes, binds to, or has immunospecificity for substantially or essentially the same, or the same, epitope or "epitopic site" on a KIR molecule as the monoclonal antibody DF200. Preferably, said KIR molecule is a KIR2DL1 human receptor or a KIR2DL2/3 human receptor.

A particular object of this invention resides in an antibody, wherein said antibody binds a common determinant present in both KIR2DL1 and KIR2DL2/3 human receptors and reverses inhibition of NK cell cytotoxicity mediated by these KIRs. The antibody more specifically binds substantially the same epitope on KIR as monoclonal antibody DF200 produced by hybridoma DF200 or antibody NKVSF1 produced by hybridoma NKVSF1, wherein the antibody is not NKVSF1.

In a preferred embodiment, the antibody of this invention is a monoclonal antibody. The most preferred antibody of this invention is monoclonal antibody DF200 produced by hybridoma DF200.

The hybridoma producing antibody DF200 has been deposited at the CNCM culture collection, as Identification no. "DF200", registration no. CNCM I-3224, registered 10 Jun. 2004, Collection Nationale de Cultures de Microorganismes, Institut Pasteur, 25, Rue du Docteur Roux, F-75724 Paris Cedex 15, France. The antibody NKVSF1 is available from Serotec (Cergy Sainte-Christophe, France), Catalog ref no. MCA2243. NKVSF1 is also referred to as pan2D mAb herein.

The invention also provides functional fragments and derivatives of the antibodies described herein, having substantially similar antigen specificity and activity (e.g., which can cross-react with the parent antibody and which potentiate the cytotoxic activity of NK cells expressing inhibitory KIR receptors), including, without limitation, a Fab fragment, a Fab'2 fragment, an immunoadhesin, a diabody, a CDR, and a ScFv. Furthermore, the antibodies of this invention may be humanized, human, or chimeric.

The invention also provides antibody derivatives comprising an antibody of the invention conjugated or covalently bound to a toxin, a radionuclide, a detectable moiety (e.g., a fluor), or a solid support.

The invention also provides pharmaceutical compositions comprising an antibody as disclosed above, a fragment thereof, or a derivative of either thereof. Accordingly, the invention also relates to use of an antibody as disclosed herein in a method for the manufacture of a medicament. In preferred embodiments, said medicament or pharmaceutical composition is for the treatment of a cancer or other proliferative disorder, an infection, or for use in transplantation.

In another embodiment, the invention provides a composition comprising an antibody that binds at least two different human inhibitory KIR receptor gene products, wherein said antibody is capable of neutralizing KIR-mediated inhibition of NK cell cytotoxicity on NK cells expressing at least one of said two different human inhibitory KIR receptors, wherein said antibody is incorporated into a liposome. Optionally said composition comprises an additional substance selected from a nucleic acid molecule for the delivery of genes for gene therapy; a nucleic acid molecule for the delivery of antisense RNA, RNAi, or siRNA for suppressing a gene in an NK cell; or a toxin or a drug for the targeted killing of NK cells additionally incorporated into said liposome.

The invention also provides methods of regulating human NK cell activity in vitro, ex vivo, or in vivo, comprising contacting human NK cells with an effective amount of an antibody of the invention, a fragment of such an antibody, a derivative of either thereof, or a pharmaceutical composition comprising at least one of any thereof. Preferred methods comprise administration of an effective amount of a pharmaceutical compositions of this invention and are directed at increasing the cytotoxic activity of human NK cells, most preferably ex vivo or in vivo, in a subject having a cancer, an infectious disease, or an immune disease.

In further aspects, the invention provides a hybridoma comprising: (a) a B cell from a mammalian host (typically a non-human mammalian host) that has been immunized with an antigen that comprises an epitope present on an inhibitory KIR polypeptide, fused to (b) an immortalized cell (e.g., a myeloma cell), wherein said hybridoma produces a monoclonal antibody binds at least two different human inhibitory KIR receptors and is capable of at least substantially neutralizing KIR-mediated inhibition of NK cell cytotoxicity in a population of NK cells expressing said at least two different human inhibitory KIR receptors. Optionally, said hybridoma does not produce monoclonal antibody NKVSF1. Preferably said antibody binds KIR2DL1 and KIR2DL2/3 receptors. Preferably said antibody binds a common determinant present on KIR2DL1 and KIR2DL2/3. Preferably said hybridoma produces an antibody that inhibits the binding of a HLA-c allele molecule having a Lys residue at position 80 to a human KIR2DL1 receptor, and the binding of a HLA-C allele molecule having an Asn residue at position 80 to human KIR2DL2/3 receptors. Preferably said hybridoma produces an antibody that binds to substantially the same epitope as monoclonal antibody DF200 produced by hybridoma DF200 on either KIR2DL1 or KIR2DL2/3 or both KIR2DL1 and KIR2DL2/3. An example of such a hybridoma is DF200.

The invention also provides methods of producing an antibody which cross-reacts with multiple KIR2DL gene products and which neutralizes the inhibitory activity of such KIRs, said method comprising the steps of:
(a) immunizing a non-human mammal with an immunogen comprising a KIR2DL polypeptide;
(b) preparing antibodies from said immunized mammal, wherein said antibodies bind said KIR2DL polypeptide,
(c) selecting antibodies of (b) that cross-react with at least two different KIR2DL gene products, and
(d) selecting antibodies of (c) that potentiate NK cells. In one embodiment, said non-human mammal is a transgenic animal engineered to express a human antibody repertoire (e.g., a non-human mammal comprising human immunoglobulin loci and native immunoglobulin gene deletions, such as a Xenomouse™ (Abgenix-Fremont, Calif., USA) or non-human mammal comprising a minilocus of human Ig-encoding genes, such as the HuMab-Mouse™ (Medarex-Princeton, N.J., USA)). Optionally, the method further comprises selecting an antibody that binds a primate, preferably a cynomolgus monkey, NK cell or KIR polypeptide. Optionally, the invention further comprises a method of evaluating an antibody, wherein an antibody produced according to the above method is administered to a primate, preferably a cynomolgus monkey, preferably wherein the monkey is observed for the presence or absence of an indication of toxicity of the antibody.

The inventors also provide a method of producing an antibody that binds at least two different human inhibitory KIR receptor gene products, wherein said antibody is capable of neutralizing KIR-mediated inhibition of NK cell cytotoxicity on a population of NK cells expressing said at least two different human inhibitory KIR receptor gene products, said method comprising the steps of:
a) immunizing a non-human mammal with an immunogen comprising an inhibitory KIR polypeptide;
b) preparing antibodies from said immunized animal, wherein said antibodies bind said KIR polypeptide,
c) selecting antibodies of (b) that cross-react with at least two different human inhibitory KIR receptor gene products, and
selecting antibodies of (c) that capable of neutralizing KIR-mediated inhibition of NK cell cytotoxicity on a population of NK cells expressing said at least two different human inhibitory KIR receptor gene products, wherein the order of steps (c) and (d) is optionally reversed and any number of the steps are optionally repeated 1 or more times. Preferably, the inhibitory KIR polypeptide used for immunization is a KIR2DL polypeptide and the antibodies selected in step (c) cross-react with at least KIR2DL1 and KIR2DL2/3. Preferably said antibody recognizes a common determinant present on at least two different KIR receptor gene products; most preferably said KIR are KIR2DL1 and KIR2DL2/3. Optionally, said method further comprises selecting an antibody that binds a primate, preferably a cynomolgus monkey, NK cell or KIR polypeptide. Optionally, the invention further comprises a method of evaluating an antibody, wherein an antibody produced according to the above method is administered to a primate, preferably a cynomolgus monkey, preferably wherein the monkey is observed for the presence or absence of an indication of toxicity of the antibody.

Optionally, in the above-described methods, the antibody selected in step c) or d) is not NKVSF1. Preferably, the antibody prepared in step (b) in the above methods is a monoclonal antibody. Preferably the antibody selected in step (c) in the above methods inhibits the binding of a HLA-C allele molecule having a Lys residue at position 80 to a human KIR2DL1 receptor, and the binding of a HLA-C allele molecule having an Asn residue at position 80 to human KIR2DL2/3 receptors. Preferably, the antibodies selected in step (d) in the above methods cause a potentiation in NK cytotoxicity, for example any substantial potentiation, or at least 5%, 10%, 20%, 30% or greater potentiation in NK cytotoxicity, e.g. at least about 50% potentiation of target NK cytotoxicity (e.g., at least about 60%, at least about 70%, at least about 80%, at least about 85%, at least about 90%, or at least about 95% (such as, for example about 65-100%) potentiation of NK cell cytotoxicity). Preferably, the antibody binds to substantially the same epitope as monoclonal antibody DF200 on KIR2DL1 and/or KIR2DL2/3. Optionally said methods also or alternatively comprise the additional step of making fragments of the selected monoclonal antibodies, making derivatives of the selected monoclonal antibodies (e.g., by conjugation with a radionuclide, cytotoxic agent, reporter molecule, or the like), or making derivatives of antibody fragments produced from or that comprise sequences that correspond to the sequences of such monoclonal antibodies.

The invention further provides a method of producing an antibody that binds at least two different human inhibitory KIR receptor gene products, wherein said antibody is capable of neutralizing KIR-mediated inhibition of NK cell cytotoxicity on a population of NK cells expressing said at least two different human inhibitory KIR receptor gene products, said method comprising the steps of:

(a) selecting, from a library or repertoire, a monoclonal antibody or an antibody fragment that cross-reacts with at least two different human inhibitory KIR2DL receptor gene products, and
(b) selecting an antibody of (a) that is capable of neutralizing KIR-mediated inhibition of NK cell cytotoxicity in a population of NK cells expressing said at least two different human inhibitory KIR2DL receptor gene products. Preferably the antibody binds a common determinant present on KIR2DL1 and KIR2DL2/3. Optionally, said antibody selected in step (b) is not NKVSF1. Preferably, the antibody selected in step (b) inhibits the binding of a HLA-c allele molecule having a Lys residue at position 80 to a human KIR2DL1 receptor, and the binding of a IILA-C allele molecule having an Asn residue at position 80 to human KIR2DL2/3 receptors. Preferably, the antibody selected in step (b) causes a potentiation in NK cytotoxicity, for example any substantial potentiation, or at least 5%, 10%, 20%, 30% or greater potentiation in NK cytotoxicity, e.g. at least about 50% potentiation of target NK cytotoxicity (e.g., at least about 60%, at least about 70%, at least about 80%, at least about 85%, at least about 90%, or at least about 95% (such as, for example about 65-100%) potentiation of NK cell cytotoxicity). Preferably, the antibody binds to substantially the same epitope as monoclonal antibody DF200 on KIR2DL1 and/or KIR2DL2/3. Optionally the method comprises the additional step of making fragments of the selected monoclonal antibodies, making derivatives of the selected monoclonal antibodies, or making derivatives of selected monoclonal antibody fragments.

Additionally, the invention provides a method of producing an antibody that binds at least two different human inhibitory KIR receptor gene products, wherein said antibody is capable of neutralizing KIR-mediated inhibition of NK cell cytotoxicity in a population of NK cells expressing said at least two different human inhibitory KIR receptor gene products, said method comprising the steps of:
a) culturing a hybridoma of the invention under conditions permissive for the production of said monoclonal antibody; and
b) separating said monoclonal antibody from said hybridoma. Optionally the method comprises the additional step of making fragments of the said monoclonal antibody, making derivatives of the monoclonal antibody, or making derivatives of such monoclonal antibody fragments. Preferably the antibody binds a common determinant present on KIR2DL1 and KIR2DL2/3.

Also provided by the present invention is a method of producing an antibody that binds at least two different human inhibitory KIR receptor gene products, wherein said antibody is capable of neutralizing KIR-mediated inhibition of NK cell cytotoxicity in a population of NK cells expressing said at least two different human inhibitory KIR receptor gene products, said method comprising the steps of:
a) isolating from a hybridoma of the invention a nucleic acid encoding said monoclonal antibody;
b) optionally modifying said nucleic acid so as to obtain a modified nucleic acid that comprises a sequence that encodes a modified or derivatized antibody comprising an amino acid sequence that corresponds to a functional sequence of the monoclonal antibody or is substantially similar thereto (e.g., is at least about 65%, at least about 75%, at least about 85%, at least about 90%, at least about 95% (such as about 70-99%) identical to such a sequence) selected from a humanized antibody, a chimeric antibody, a single chain antibody, an immunoreactive fragment of an antibody, or a fusion protien comprising such an immunoreactive fragment;
c) inserting said nucleic acid or modified nucleic acid (or related nucleic acid coding for the same amino acid sequence) into an expression vector, wherein said encoded antibody or antibody fragment is capable of being expressed when said expression vector is present in a host cell grown under appropriate conditions;
d) transfecting a host cell with said expression vector, wherein said host cell does not otherwise produce immunoglobulin protein;
e) culturing said transfected host cell under conditions which cause the expression of said antibody or antibody fragment; and
f) isolating the antibody or antibody fragment produced by said transfected host cell. Preferably the antibody hinds a common determinant present on KIR2DL1 and KIR2DL2/3.

It will be appreciated that the invention also provides a composition comprising an antibody that binds at least two different human inhibitory KIR receptor gene products, wherein said antibody is capable of neutralizing KIR-mediated inhibition of NK cell cytotoxicity in NK cells expressing at least one of said two different human inhibitory KIR receptors, said antibody being present in an amount effective to detectably potentiate NK cell cytotoxicity in a patient or in a biological sample comprising NK cells; and a pharmaceutically acceptable carrier or excipient. Preferably the antibody binds a common determinant present on KIR2DL1 and KIR2DL2/3. Said composition may optionally further comprise a second therapeutic agent selected from, for example, an immunomodulatory agent, a hormonal agent, a chemotherapeutic agent, an anti-angiogenic agent, an apoptotic agent, a second antibody that binds to and inhibits an inhibitory KIR receptor, an anti-infective agent, a targeting agent, or an adjunct compound. Advantageous immunomodulatory agents may be selected from IL-1alpha, IL-1beta, IL-2, IL-3, IL-4, IL-5, IL-6, IL-7, IL-8, IL-9, IL-10, IL-11, IL-12, IL-13, IL-15, IL-21, TGF-beta, GM-CSF, M-CSF, G-CSF, TNF-alpha, TNF-beta, LAF, TCGF, BCGF, TRF, BAF, BDG, MP, LIF, OSM, TMF, PDGF, IFN-alpha, IFN-beta, or IFN-gamma. Examples of said chemotherapeutic agents include alkylating agents, antimetabolites, cytotoxic antibiotics, adriamycin, dactinomycin, mitomycin, carminomycin, daunomycin, doxorubicin, tamoxifen, taxol, taxotere, vincristine, vinblastine, vinorelbine, etoposide (VP-16), 5-fluorouracil (5FU), cytosine arabinoside, cyclophosphamide, thiotepa, methotrexate, camptothecin, actinomycin-D, mitomycin C, cisplatin (CDDP), aminopterin, combretastatin(s), other vinca alkyloids and derivatives or prodrugs thereof. Examples of hormonal agents include leuprorelin, goserelin, triptorelin, buserelin, tamoxifen, toremifene, flutamide, nilutamide, cyproterone bicalutamid anastrozole, exemestane, letrozole, fadrozole medroxy, chlormadinone, megestrol, other LHRH agonists, other anti-estrogens, other anti-androgens, other aromatase inhibitors, and other progestagens. Preferably, said second antibody that binds to and inhibits an inhibitory KIR receptor is an antibody or a derivative or fragment thereof that binds to an epitope of an inhibitory KIR receptor that differs from the epitope bound by said antibody that binds a common determinant present on at least two different human inhibitory KIR receptor gene products.

The invention further provides a method of detectably potentiating NK cell activity in a patient in need thereof; comprising the step of administering to said patient a composition according to the invention. A patient in need of NK cell activity potentiation can be any patient having a disease or disorder wherein such potentiation may promote, enhance, and/or induce a therapeutic effect (or promotes, enhances, and/or induces such an effect in at least a substantial proportion of patients with the disease or disorder and substantially similar characteristics as the patient—as may determined by, e.g., clinical trials). A patient in need of such treatment may be suffering from, e.g., cancer, another proliferative disorder, an infectious disease or an immune disorder. Preferably said method comprises the additional step of administering to said patient an appropriate additional therapeutic agent selected from an immunomodulatory agent, a hormonal agent, a chemotherapeutic agent, an anti-angiogenic agent, an apoptotic agent, a second antibody that binds to and inhibits an inhibitory KIR receptor, an anti-infective agent, a targeting agent or an adjunct compound wherein said additional therapeutic agent is administered to said patient as a single dosage form together with said antibody, or as separate dosage form. The dosage of the antibody (or antibody fragment/derivative) and the dosage of the additional therapeutic agent collectively are sufficient to detectably induce, promote, and/or enhance a therapeutic response in the patient which comprises the potentiation of NK cell activity. Where administered separately, the antibody, fragment, or derivative and the additional therapeutic agent are desirably administered under conditions (e.g., with respect to timing, number of doses, etc.) that result in a detectable combined therapeutic benefit to the patient.

Further encompassed by the present invention are antibodies of the invention which are capable of specifically binding non-human primate, preferably monkey, NK cells and/or monkey KIR receptors. Also encompassed are methods for evaluating the toxicity, dosage and/or activity or efficacy of antibodies of the invention which are candidate medicaments. In one aspect, the invention encompasses a method for determining a dose of an antibody that is toxic to an animal or target tissue by administering an antibody of the invention to an non-human primate recipient animal having NK cells, and assessing any toxic or deleterious or adverse effects of the agent on the animal, or preferably on a target tissue. In another aspect, the invention is a method for identifying an antibody that is toxic to an animal or target tissue by administering an antibody of the invention to an non-human primate recipient animal having NK cells, and assessing any toxic or deleterious or adverse effects of the agent on the animal, or preferably on a target tissue. In another aspect, the invention is a method for identifying an antibody that is efficacious in treatment of an infected, disease or tumor by administering an antibody of the invention to a non-human primate model of infection, disease or cancer, and identifying the antibody that ameliorates the infection, disease or cancer, or a symptom thereof. Preferably said antibody of the invention is an antibody which (a) cross reacts with at least two inhibitory human KIR receptors at the surface of human NK cells, and (b) cross-reacts with NK cells or a KIR receptor of the non-human primate.

Further encompassed by the present invention is a method of detecting the presence of NK cells bearing an inhibitory KIR on their cell surface in a biological sample or a living organism, said method comprising the steps of:
  a) contacting said biological sample or living organism with an antibody of the invention, wherein said antibody is conjugated or covalently bound to a detectable moiety; and b) detecting the presence of said antibody in said biological sample or living organism.

The invention also provides a method of purifying from a sample NK cells bearing an inhibitory KIR on their cell surface comprising the steps of:
  a) contacting said sample with an antibody of the invention under conditions that allow said NK cells bearing an inhibitory KIR on their cell surface to bind to said antibody, wherein said antibody is conjugated or covalently bound to a solid support (e.g., a bead, a matrix, etc.); and
  b) eluting said bound NK cells from said antibody conjugated or covalently bound to a solid support.

In a further aspect, the invention provides an antibody, antibody fragment, or derivative of either thereof, that comprises the light variable region or one or more light variable region CDRs of antibody DF200 or antibody Pan2D as illustrated in FIG. 12. In still another aspect, the invention provides an antibody, antibody fragment, or derivative of either thereof that comprises a sequence that is highly similar to all or essentially all of the light variable region sequence of DF200 or Pan2D or one or more of the light variable region CDRs of one or both of these antibodies.

In a further aspect, the invention provides an antibody, antibody fragment, or derivative of either thereof, that comprises the heavy variable region or one or more light variable region CDRs of antibody DF200 as illustrated in FIG. 13. In still another aspect, the invention provides an antibody, antibody fragment, or derivative of either thereof that comprises a sequence that is highly similar to all or essentially all of the heavy variable region sequence of DF200.

These and additional advantageous aspects and features of the invention may be further described elsewhere herein.

BRIEF DESCRIPTION OF THE DRAWINGS

FIG. 4 depicts reconstitution of cell lysis by NK clones of HLA Cw4 positive target cells in the presence of F(ab')2 fragments of the DF200 and EB6 antibodies.

FIGS. 5 and 6 depict monoclonal antibodies DF200, NKVSF1 (pan2D), human antibodies 1-7F9, 1-4F1, 1-6F5 and 1-6F1, and KIR2DL1 or KIR2DL2/3 specific conventional antibodies neutralizing the KIR2DL-mediated inhibition of KIR2DL1 positive NK cell cytotoxicity on Cw4 positive target cells (Cw4 transfected cells in FIG. 5 and EBV cells in FIG. 6).

FIGS. 11A and 11B illustrate the interaction between KIR-Fc fusion proteins and cells or KIR-specific monoclonal antibodies. FIG. 11A utilizes FACS for studying the interaction between KIR-Fc fusion proteins and cells. FIG. 11B demonstrates the binding of KIR-specific monclonal antibodies with KIR2DL1(R131W)-hFc and KIR2DL1-hFc.

FIG. 12 provides a comparative alignment of the amino acid sequences of the light variable regions and light variable region CDRs of antibodies DF200 and Pan2D mAb.

FIG. 13 provides the heavy variable region of antibody DF200.

DETAILED DESCRIPTION OF THE INVENTION

Antibodies

Figure 1:
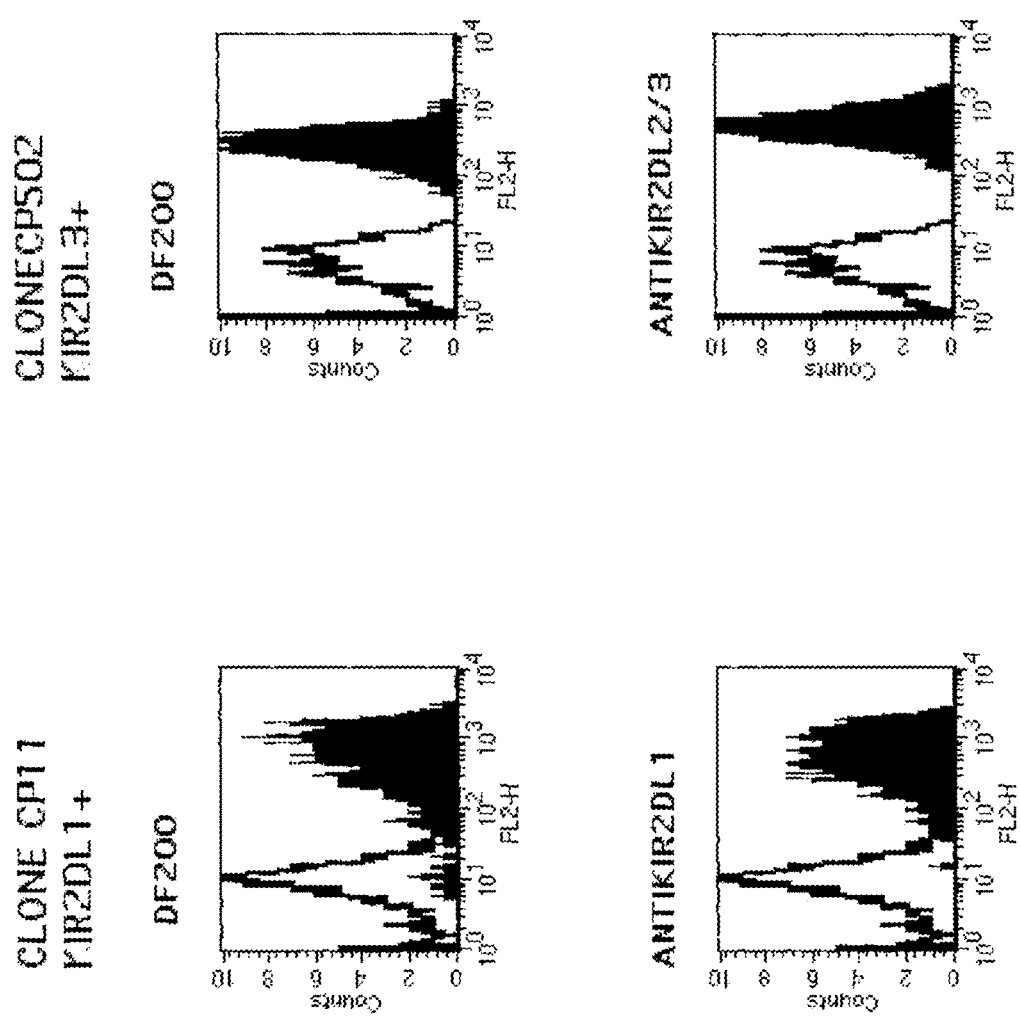
FIG. 1 depicts monoclonal antibody DF200 binding to a common determinant of various human KIR2DL receptors.

The present invention provides novel antibodies and fragments or derivatives thereof that bind common determinants of human inhibitory KIR receptors, preferably a determinant present on at least two different KIR2DL gene products, and cause potentiation of NK cells expressing at least one of those KIR receptors. The invention discloses, for the first time, that such cross-reacting and neutralizing antibodies can be produced, which represents an unexpected result and opens an avenue towards novel and effective NK-based therapies, particularly in human subjects. In a preferred embodiment, the antibody is not monoclonal antibody NKVSF1.

Within the context of this invention a "common determinant" designates a determinant or epitope that is shared by several gene products of the human inhibitory KIR receptors. Preferably, the common determinant is shared by at least two members of the KIR2DL receptor group. More preferably, the determinant is shared by at least KIR2DL1 and KIR2DL2/3. Certain antibodies of this invention may, in addition to recognizing multiple gene products of KIR2DL, also recognize determinants present on other inhibitory KIRs, such as gene product of the KIR3DL receptor group. The determinant or epitope may represent a peptide fragment or a conformational epitope shared by said members. In a more specific embodiment, the antibody of this invention specifically binds to substantially the same epitope recognized by monoclonal antibody DF200. This determinant is present on both KIR2DL1 and KIR2DL2/3.

Within the context of this invention, the term antibody that "binds" a common determinant designates an antibody that binds said determinant with specificity and/or affinity.

The term "antibody," as used herein, refers to polyclonal and monoclonal antibodies, as well as to fragments and derivatives of said polyclonal and monoclonal antibodies unless otherwise stated or clearly contradicted by context. Depending on the type of constant domain in the heavy chains, full length antibodies typically are assigned to one of five major classes: IgA, IgD, IgE, IgG, and IgM. Several of these are further divided into subclasses or isotypes, such as IgG1, IgG2, IgG3, IgG4, and the like. The heavy-chain constant domains that correspond to the difference classes of immunoglobulins are termed "alpha," "delta," "epsilon," "gamma" and "mu," respectively. The subunit structures and three-dimensional configurations of different classes of immunoglobulins are well known. IgG and/or IgM are the preferred classes of antibodies employed in this invention because they are the most common antibodies in the physiological situation and because they are most easily made in a laboratory setting. Preferably the antibody of this invention is a monoclonal antibody. Because one of the goals of the invention is to block the interaction of an inhibitory KIR and its corresponding HLA ligand in vivo without depleting the NK cells, isotypes corresponding to Fc receptors that mediate low effector function, such as IgG4, typically are preferred.

The antibodies of this invention may be produced by a variety of techniques known in the art. Typically, they are produced by immunization of a non-human animal, preferably a mouse, with an immunogen comprising an inhibitory KIR polypeptide, preferably a KIR2DL polypeptide, more preferably a human KIR2DL polypeptide. The inhibitory KIR polypeptide may comprise the full length sequence of a human inhibitory KIR polypeptide, or a fragment or derivative thereof, typically an immunogenic fragment, i.e., a portion of the polypeptide comprising an epitope exposed on the surface of the cell expressing an inhibitory KIR receptor. Such fragments typically contain at least about 7 consecutive amino acids of the mature polypeptide sequence, even more preferably at least about 10 consecutive amino acids thereof. Fragments typically are essentially derived from the extra-cellular domain of the receptor. Even more preferred is a human KIR2DL polypeptide which includes at least one, more preferably both, extracellular Ig domains, of the full length KIRDL polypeptide and is capable of mimicking at least one conformational epitope present in a KIR2DL receptor. In other embodiments, said polypeptide comprises at least about 8 consecutive amino acids of an extracellular Ig domain of amino acid positions 1-224 of the KIR2DL1 polypeptide (amino acid numbering of according to PROW website describing the KIR gene family, http://www.nebi.nlm.nih.gov/prow/guide/1326018082.htm)

In a most preferred embodiment, the immunogen comprises a wild-type human KIR2DL polypeptide in a lipid membrane, typically at the surface of a cell. In a specific embodiment, the immunogen comprises intact NK cells, particularly intact human NK cells, optionally treated or lysed.

The step of immunizing a non-human mammal with an antigen may be carried out in any manner well known in the art for stimulating the production of antibodies in a mouse (see, for example, E. Harlow and D. Lane, Antibodies: A Laboratory Manual, Cold Spring Harbor Laboratory Press, Cold Spring Harbor, N.Y. (1988)). The immunogen is then suspended or dissolved in a buffer, optionally with an adjuvant, such as complete Freund's adjuvant. Methods for determining the amount of immunogen, types of buffers and amounts of adjuvant are well known to those of skill in the art and are not limiting in any way on the present invention. These parameters may be different for different immunogens, but are easily elucidated.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be utilized as long as they result in the production of B cells expressing an antibody directed to the antigen used in immunization.

For polyclonal antibody preparation, serum is obtained from an immunized non-human animal and the antibodies present therein isolated by well-known techniques. The serum may be affinity purified using any of the immunogens set forth above linked to a solid support so as to obtain antibodies that react with inhibitory KIR receptors.

In an alternate embodiment, lymphocytes from an unimmunized non-human mammal are isolated, grown in vitro, and then exposed to the immunogen in cell culture. The lymphocytes are then harvested and the fusion step described below is carried out.

For monoclonal antibodies, the next step is the isolation of splenocytes from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule and through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the lymphocytes can be fused to an immortal cell line. This is typically a mouse myeloma cell line, although many other immortal cell lines useful for creating hybridomas are known in the art. Preferred marine myeloma lines include, but are not limited to, those derived from MOPC-21 and MPC-11 mouse tumors available from the Salk Institute Cell Distribution Center, San Diego, Calif. U.S.A., X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Hybridomas are typically grown on a feeder layer of macrophages. The macrophages are preferably from littermates of the non-human mammal used to isolate splenocytes and are typically primed with incomplete Freund's adjuvant or the like several days before plating the hybridomas. Fusion methods are described in Goding, "Monoclonal Antibodies: Principles and Practice," pp. 59-103 (Academic Press, 1986), the disclosure of which is herein incorporated by reference.

The cells are allowed to grow in the selection media for sufficient time for colony formation and antibody production. This is usually between about 7 and about 14 days. The hybridoma colonies are then assayed for the production of antibodies that cross-react with multiple inhibitory KIR receptor gene products. The assay is typically a colorimetric ELISA-type assay, although any assay may be employed that can be adapted to the wells that the hybridomas are grown in. Other assays include immunoprecipitation and radioimmunoassay. The wells positive for the desired antibody production are examined to determine if one or more distinct colonies are present. If more than one colony is present, the cells may be re-cloned and grown to ensure that only a single cell has given rise to the colony producing the desired antibody. Positive wells with a single apparent colony are typically re-cloned and re-assayed to insure only one monoclonal antibody is being detected and produced.

Antibodies may also be produced by selection of combinatorial libraries of immunoglobulins, as disclosed for instance in Ward et al., *Nature,* 341 (1989) p. 544).

The antibodies of this invention are able to neutralize the KIR-mediated inhibition of NK cell cytotoxicity; particularly inhibition mediated by KIR2DL receptors and more particularly at least both the KIR2DL1 and KIR2DL2/3 inhibition. These antibodies are thus "neutralizing" or "inhibitory" antibodies, in the sense that they block, at least partially and detectably, the inhibitory signaling pathway mediated by KIR receptors when they interact with MHC class I molecules. More importantly, this inhibitory activity is displayed with respect to several types of inhibitory KIR receptors, preferably several KIR2DL receptor gene products, and more preferably at least both KIR2DL1 and KIR2DL2/3 so that these antibodies may be used in various subjects with high efficacy. Inhibition of KIR-mediated inhibition of NK cell cytotoxicity can be assessed by various assays or tests, such as binding or cellular assays.

Once an antibody that cross-reacts with multiple inhibitor KIR receptors is identified, it can be tested for its ability to neutralize the inhibitory effect of those KIR receptors in intact NK cells. In a specific variant, the neutralizing activity can be illustrated by the capacity of said antibody to reconstitute lysis by KIR2DL-positive NK clones of HLA-C positive targets. In another specific embodiment, the neutralizing activity of the antibody is defined by the ability of the antibody to inhibit the binding of HLA-C molecules to KIR2DL1 and KIR2DL3 (or the closely related KIR2DL2) receptors, further preferably as it is the capacity of the antibody to alter:

the binding of a HLA-C molecule selected from Cw1, Cw3, Cw7, and Cw8 (or of a HLA-C molecule having an Asn residue at position 80) to KIR2DL2/3; and the binding of a HLA-C molecule selected from Cw2, Cw4, Cw5 and Cw6 (or of a HLA-C molecule having a Lys residue at position 80) to KIR2DL1.

In another variant, the inhibitory activity of an antibody of this invention can be assessed in a cell based cytotoxicity assay, as disclosed in the Examples provided herein.

In another variant, the inhibitory activity of an antibody of this invention can be assessed in a cytokine-release assay, wherein NK cells are incubated with the test antibody and a target cell line expressing one HLA-C allele recognized by a KIR molecule of the NK population, to stimulate NK cell cytokine production (for example IFN-γ and/or GM-CSF production). In an exemplary protocol, IFN-γ production from PBMC is assessed by cell surface and intracytoplasmic staining and analysis by flow cytometry after about 4 days in culture. Briefly, Brefeldin A (Sigma Aldrich) can be added at a final concentration of about 5 µg/ml for the least about 4 hours of culture. The cells can then incubated with anti-CD3 and anti-CD56 mAb prior to permeabilization (IntraPrep™; Beckman Coulter) and staining with PE-anti-IFN-γ or PE-IgG1 (Pharmingen). GM-CSF and IFN-γ production from polyclonal activated NK cells can be measured in supernatants using ELISA (GM-CSF: DuoSet Elisa, R&D Systems, Minneapolis, Minn.; IFN-γ: OptE1A set, Pharmingen).

Antibodies of this invention may partially or fully neutralize the KIR-mediated inhibition of NK cell cytotoxicity. The term "neutralize KIR-mediated inhibition of NK cell cytotoxicity," as used herein means the ability to increase to at least about 20%, preferably to at least about 30%, at least about 40%, at least about 50% or more (e.g., about 25-100%) of specific lysis obtained at the same ratio with NK cells or NK cell lines that are not blocked by their KIR, as measured by a classical chromium release test of cytotoxicity, compared with the level of specific lysis obtained without antibody when an NK cell population expressing a given KIR is put in contact with a target cell expressing the cognate MHC class I molecule (recognized by the KIR expressed on NK cell). For example, preferred antibodies of this invention are able to induce the lysis of matched or HLA compatible or autologous target cell populations, i.e., cell populations that would not be effectively lysed by NK cells in the absence of said antibody. Accordingly, the antibodies of this invention may also be defined as facilitating NK cell activity in vivo.

Alternatively, the term "neutralize KIR mediated inhibition" means that in a chromium assay using an NK cell clone or transfectant expressing one or several inhibitory KIRs and a target cell expressing only one HLA allele that is recognized by one of the KIRs on the NK cell, the level of cytotoxicity obtained with the antibody should be at least about 20%, preferably at least about 30%, at least about 40%, at least about 50% (e.g., about 25-100%), or more of the cytotoxicity obtained with a known blocking anti MHC class I molecule, such as W6/32 anti MHC class I antibody.

In a specific embodiment, the antibody binds substantially the same epitope as monoclonal antibody DF200 (produced by hybridoma DF200). Such antibodies are referred to herein as "DF200 like antibodies." In a further preferred embodiment, the antibody is a monoclonal antibody. More preferred "DF200 like antibodies" of this invention are antibodies other than the monoclonal antibody NKVSF1. Most preferred is monoclonal antibody DF200 (produced by hybridoma DF200).

The term "binds to substantially the same epitope or determinant as" an antibody of interest means that an antibody "competes" with said antibody of interest. The term "binds to substantially the same epitope or determinant as" the monoclonal antibody DF200 means that an antibody "competes" with DF200. Generally, an antibody that "binds to substantially the same epitope or determinant as" the monoclonal antibody of interest (e.g. DF200, NKVSF1, 17F9) means that the antibody "competes" with said antibody of interest for any one of more KIR molecules, preferably a KIR molecule selected from the group consisting of KIR2DL1 and KIR2DL2/3. In other examples, an antibody that binds to substantially the same epitope or determinant on a KIR2DL1 molecule as the antibody of interest "competes" with the antibody of interest for binding to KIR2DL1. An antibody that binds to substantially the same epitope or determinant on a KIR2DL2/3 molecule as the antibody of interest "competes" with antibody of interest for binding to KIR2DL2/3.

The term "binds to essentially the same epitope or determinant as" an antibody of interest means that an antibody "competes" with said antibody of interest for any and all KIR molecules to which said antibody of interest specifically binds. The term "binds to essentially the same epitope or determinant as" the monoclonal antibody DF200 means that an antibody "competes" with DF200 for any and all KIR molecules to which DF200 specifically binds. For example, an antibody that hinds to essentially the same epitope or determinant as the monoclonal antibodies DF200 or NKVSF1 "competes" with said DF200 or NKVSF1 respectively for binding to KIR2DL1, KIR2DL2/3, KIR2DS1 and KIR2DS2.

The identification of one or more antibodies that bind(s) to substantially or essentially the same epitope as the monoclonal antibodies described herein can be readily determined using any one of variety of immunological screening assays in which antibody competition can be assessed. A number of such assays are routinely practiced and well known in the art (see, e.g., U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control (DF200, for example) and test antibodies are admixed (or pre-adsorbed) and applied to a sample containing both KIR2DL1 and KIR2DL2/3, each of which is known to be bound by DF200. Protocols based upon ELISAs, radioimmunoassays, Western blotting, and the use of BIACORE analysis (as set forth, for example, in the Examples section) are suitable for use in such simple competition studies.

In certain embodiments, one would pre-mix the control antibodies (DF200, for example) with varying amounts of the test antibodies (e.g., about 1:10 or about 1:100) for a period of time prior to applying to the inhibitory KIR antigen sample. In other embodiments, the control and varying amounts of test antibodies can simply be admixed during exposure to the KIR antigen sample. As long as one can distinguish bound from free antibodies (e.g., by using separation or washing techniques to eliminate unbound antibodies) and DF200 from the test antibodies (e.g., by using species-specific or isotype-specific secondary antibodies or by specifically labeling DF200 with a detectable label) one will be able to determine if the test antibodies reduce the binding of DF200 to the two different KIR2DL antigens, indicating that the test antibody recognizes substantially the same epitope as DF200. The binding of the (labeled) control antibodies in the absence of a completely irrelevant antibody can serve as the control high value. The control low value can be obtained by incubating the labeled (DF200) antibodies with unlabelled antibodies of exactly the same type (DF200), where competition would occur and reduce binding of the labeled antibodies. In a test assay, a significant reduction in labeled antibody reactivity in the presence of a test antibody is indicative of a test antibody that recognizes substantially the same epitope, i.e., one that "cross-reacts" with the labeled (DF200) antibody. Any test antibody that reduces the binding of DF200 to each of KIR2DL1 and KIR2DL2/3 antigens by at least about 50%, such as at least about 60%, or more preferably at least about 70% (e.g., about 65-100%), at any ratio of DF200:test antibody between about 1:10 and about 1:100 is considered to be an antibody that binds to substantially the same epitope or determinant as DF200. Preferably, such test antibody will reduce the binding of DF200 to each of the KIR2DL antigens by at least about 90% (e.g., about 95%).

Competition can be assessed by, for example, a flow cytometry test. In such a test, cells bearing a given KIR can be incubated first with DF200, for example, and then with the test antibody labeled with a fluorochrome or biotin. The antibody is said to compete with DF200 if the binding obtained upon preincubation with saturating amount of DF200 is about 80%, preferably about 50%, about 40% or less (e.g., about 30%) of the binding (as measured by mean of fluorescence) obtained by the antibody without preincubation with DF200. Alternatively, an antibody is said to compete with DF200 if the binding obtained with a labeled DF200 (by a fluorochrome or biotin) on cells preincubated with saturating amount of test antibody is about 80%, preferably about 50%, about 40%, or less (e.g., about 30%) of the binding obtained without preincubation with the antibody.

A simple competition assay in which a test antibody is pre-adsorbed and applied at saturating concentration to a surface onto which both KIR2DL1 and KIR2DL2/3 are immobilized also may be advantageously employed. The surface in the simple competition assay is preferably a BIACORE chip (or other media suitable for surface plasmon resonance analysis). The control antibody (e.g., DF200) is then brought into contact with the surface at KIR2DL1 and KIR2DL2/3-saturating concentration and the KIR2DL1 and KIR2DL2/3 surface binding of the control antibody is measured. This binding of the control antibody is compared with the binding of the control antibody to the KIR2DL1 and KIR2DL2/3-containing surface in the absence of test antibody. In a test assay, a significant reduction in binding of the KIR2DL1 and KIR2DL2/3-containing surface by the control antibody in the presence of a test antibody indicates that the test antibody recognizes substantially the same epitope as the control antibody such that the test antibody "cross-reacts" with the control antibody. Any test antibody that reduces the binding of control (such as DF200) antibody to each of KIR2DL1 and KIR2DL2/3 antigens by at least about 30% or more preferably about 40% can be considered to be an antibody that binds to substantially the same epitope or determinant as a control (e.g., DF200). Preferably, such test antibody will reduce the binding of the control antibody (e.g., DF200) to each of the KIR2DL antigens by at least about 50% (e.g., at least about 60%, at least about 70%, or more). It will be appreciated that the order of control and test antibodies can be reversed: that is the control antibody can be first bound to the surface and the test antibody is brought into contact with the surface thereafter in a competition assay. Preferably, the antibody having higher affinity for KIR2DL1 and KIR2DL2/3 antigens is bound to the KIR2DL1 and KIR2DL2/3-containing surface first, as it will be expected that the decrease in binding seen for the second antibody (assuming the antibodies are cross-reacting) will be of greater magnitude. Further examples of such assays are provided in the Examples and in, e.g., Saunal and Regenmortel, (1995) J. Immunol. Methods 183: 33-41, the disclosure of which is incorporated herein by reference.

While described in the context of DF200 for the purposes of exemplification, it will be appreciated that the above-described immunological screening assays can also be used to identify antibodies that compete with NKVSF1, 1-7F9, EB6, GL183, and other antibodies according to the invention.

Upon immunization and production of antibodies in a vertebrate or cell, particular selection steps may be performed to isolate antibodies as claimed. In this regard, in a specific embodiment, the invention also relates to methods of producing such antibodies, comprising:
(a) immunizing a non-human mammal with an immunogen comprising an inhibitory KIR polypeptide;
(b) preparing antibodies from said immunized animal, wherein said antibodies bind said KIR polypeptide,
(c) selecting antibodies of (b) that cross-react with at least two different inhibitory KIR gene products, and
(d) selecting antibodies of (c) that are capable of neutralizing KIR-mediated inhibition of NK cell cytotoxicity on a population of NK cells expressing said at least two different human inhibitory KIR receptor gene products.

The selection of an antibody that cross-reacts with at least two different inhibitory KIR gene products may be achieved by screening the antibody against two or more different inhibitory KIR antigens, for example as described above.

In a more preferred embodiment, the antibodies prepared in step (b) are monoclonal antibodies. Thus, the term "preparing antibodies from said immunized animal," as used herein, includes obtaining B-cells from an immunized animal and using those B cells to produce a hybridoma that expresses antibodies, as well as obtaining antibodies directly from the serum of an immunized animal. In another preferred embodiment, the antibodies selected in step (c) are those that cross-react with at least KIR2DL1 and KIR2DL2/3.

In yet another preferred embodiment, the antibodies selected in step (d) cause at least about 10% specific lysis mediated by NK cells displaying at least one KIR recognized by the antibody, and preferably at least about 40% specific lysis, at least about 50% specific lysis, or more preferably at least about 70% specific lysis (e.g., about 60-100% specific lysis), as measured in a standard chromium release assay, towards a target cell expressing cognate HLA class I molecule, compared with the lysis or cytotoxicity obtained at the same effector/target ratio with NK cells that are not blocked by their KIR. Alternatively, the antibodies selected in step (d) when used in a chromium assay employing an NK cell clone expressing one or several inhibitory KIRs and a target cell expressing only one HLA allele that is recognized by one of the KIRs on the NK clone, the level of cytotoxicity obtained with the antibody should be at least about 20% preferably at least about 30%, or more of the cytotoxicity obtained with a blocking anti MHC class I mAb such as W6/32 anti MHC class I antibody.

The order of steps (c) and (d) of the immediately above-described method can be changed. Optionally, the method also or alternatively may further comprise additional steps of making fragments of the monoclonal antibody or derivatives of the monoclonal antibody or such fragments, e.g., as described elsewhere herein.

In a preferred embodiment, the non-human animal used to produce antibodies according to applicable methods of the invention is a mammal, such as a rodent (e.g., mouse, rat, etc.), bovine, porcine, horse, rabbit, goat, sheep, etc. Also, the non-human mammal may be genetically modified or engineered to produce "human" antibodies, such as the Xenomouse™ (Abgenix) or HuMAb-Mouse™ (Medarex).

In another variant, the invention provides a method for obtaining an antibody that comprises:
(a) selecting, from a library or repertoire, a monoclonal antibody, a fragment of a monoclonal antibody, or a derivative of either thereof that cross-reacts with at least two different human inhibitory KIR2DL receptor gene products, and
(b) selecting an antibody, fragment, or derivative of (a) that is capable of neutralizing KIR-mediated inhibition of NK cell cytotoxicity on a population of NK cells expressing said at least two different human inhibitory KIR2DL receptor gene products.

The repertoire may be any (recombinant) repertoire of antibodies or fragments thereof; optionally displayed by any suitable structure (e.g., phage, bacteria, synthetic complex, etc.). Selection of inhibitory antibodies may be performed as disclosed above and further illustrated in the examples.

According to another embodiment, the invention provides a hybridoma comprising a B cell from a non-human host, wherein said B cell produces an antibody that binds a determinant present on at least two different human inhibitory KIR receptor gene products and said antibody is capable of neutralizing the inhibitory activity of said receptors. More preferably, the hybridoma of this aspect of the invention is not a hybridoma that produces the monoclonal antibody NKVSF1. The hybridoma according to this aspect of the invention can be created as described above by the fusion of splenocytes from the immunized non-human mammal with an immortal cell line. Hybridomas produced by this fusion can be screened for the presence of such a cross-reacting antibody as described elsewhere herein. Preferably, the hybridoma produces an antibody the recognizes a determinant present on at least two different KIR2DL gene products, and cause potentiation of NK cells expressing at least one of those KIR receptors. Even more preferably, the hybridoma produces an antibody that binds to substantially the same epitope or determinant as DF200 and which potentiates NK cell activity. Most preferably, that hybridoma is hybridoma DF200 which produces monoclonal antibody DF200.

Hybridomas that are confirmed to produce a monoclonal antibody of this invention can be grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Amersham Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

According to an alternate embodiment, the DNA encoding an antibody that binds a determinant present on at least two different human inhibitory KIR receptor gene products, is isolated from the hybridoma of this invention and placed in an appropriate expression vector for transfection into an appropriate host. The host is then used for the recombinant production of the antibody, or variants thereof, such as a humanized version of that monoclonal antibody, active fragments of the antibody, or chimeric antibodies comprising the antigen recognition portion of the antibody. Preferably, the DNA used in this embodiment encodes an antibody that recognizes a determinant present on at least two different KIR2DL gene products, and cause potentiation of NK cells expressing at least one of those KIR receptors. Even more preferably, the DNA encodes an antibody that binds to substantially the same epitope or determinant as DF200 and which potentiates NK cell activity. Most preferably, that DNA encodes monoclonal antibody DF200.

DNA encoding the monoclonal antibodies of the invention is readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant expression in bacteria of DNA encoding the antibody is well known in the art (see, for example, Skerra et al., *Curr. Opinion in Immunol.*, 5, pp. 256 (1993); and Pluckthun, *Immunol. Revs.*, 130, pp. 151 (1992).

Fragments and Derivatives of a Monoclonal Antibody

Fragments and derivatives of antibodies of this invention (which are encompassed by the term "antibody" or "antibodies" as used in this application, unless otherwise stated or clearly contradicted by context), preferably a DF-200-like antibody, can be produced by techniques that are known in the art. "Immunoreactive fragments" comprise a portion of the intact antibody, generally the antigen binding site or variable region. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multi specific antibodies formed from antibody fragments. For instance, Fab or F(ab')2 fragments may be produced by protease digestion of the isolated antibodies, according to conventional techniques. It will be appreciated that immunoreactive fragments can be modified using known methods, for example to slow clearance in vivo and obtain a more desirable pharmacokinetic profile the fragment may be modified with polyethylene glycol (PEG). Methods for coupling and site-specifically conjugating PEG to a Fab' fragment are described in, for example, Leong et al, *Cytokine* 16(3):106-119 (2001) and Delgado et al, *Br. J. Cancer* 73(2):175-182 (1996), the disclosures of which are incorporated herein by reference.

In a particular aspect, the invention provides antibodies, antibody fragments, and antibody derivatives comprising the light chain variable region sequence of DF-200 as set forth in FIG. 12. In another particular aspect, the invention provides antibodies, antibody fragments, and antibody derivatives that comprise the light chain variable region sequence of Pan2D as set forth in FIG. 12. In another aspect, the invention provides antibodies, antibody fragments, and derivatives thereof that comprise one or more of the light variable region CDRs of DF-200 as set forth in FIG. 12. In yet another aspect, the invention provides antibodies, antibody fragments, and derivatives thereof that comprise one or more light variable region CDRs of Pan2D as set forth in FIG. 12. Functional variants/analogs of such sequences can be generated by making suitable substitutions, additions, and/or deletions in these disclosed amino acid sequences using standard techniques, which may be aided by the comparison of the sequences. Thus, for example, CDR residues that are conserved between Pan2D and DF-200 may be suitable targets for modification inasmuch as such residues may not contribute to the different profiles in competition these antibodies have with respect to other antibodies disclosed herein (although Pan2D and DF-200 do compete) and thus may not contribute to the specificity of these antibodies for their particular respective epitopes. In another aspect, positions where a residue is present in a sequence of one of these antibodies, but not another, may be suitable for deletions, substitutions, and/or insertions.

In a particular aspect, the invention provides antibodies, antibody fragments, and antibody derivatives comprising the heavy chain variable region sequence of DF-200 as set forth in FIG. 13. In another aspect, the invention provides antibodies, antibody fragments, and derivatives thereof that comprise one or more of the heavy variable region CDRs of DF-200 as set forth in FIG. 13. Functional variants/analogs of such sequences can be generated by making suitable substitutions, additions, and/or deletions in these disclosed amino acid sequences using standard techniques, which may be aided by the comparison of the sequences. In another aspect, positions where a residue is present in a sequence of one of these antibodies, but not another, may be suitable for deletions, substitutions, and/or insertions.

Alternatively, the DNA of a hybridoma producing an antibody of this invention, preferably a DF-200-like antibody, may be modified so as to encode for a fragment of this invention. The modified DNA is then inserted into an expression vector and used to transform or transfect an appropriate cell, which then expresses the desired fragment.

In an alternate embodiment, the DNA of a hybridoma producing an antibody of this invention, preferably a DF-200-like antibody, can be modified prior to insertion into an expression vector, for example, by substituting the coding sequence for human heavy- and light-chain constant domains in place of the homologous non-human sequences (e.g., Morrison et al., *Proc. Natl. Acad. Sci. U.S.A.*, 81, pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody of the invention.

Thus, according to another embodiment, the antibody of this invention, preferably a DF-200-like antibody, is humanized. "Humanized" forms of antibodies according to this invention are specific chimeric immunoglobulins, immunoglobulin chains or fragments thereof (such as Fv, Fab, Fab', F(ab')$_2$, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody. In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fe), typically that of a human immunoglobulin. For further details see Jones et al., *Nature,* 321, pp. 522 (1986); Reichmann et al., *Nature,* 332, pp. 323 (1988); and Presta, *Curr. Op. Struct. Biol.,* 2, pp. 593 (1992).

Methods for humanizing the antibodies of this invention are well known in the art. Generally, a humanized antibody according to the present invention has one or more amino acid residues introduced into it from the original antibody. These murine or other non-human amino acid residues are often referred to as "import" residues, which are typically taken from an "import" variable domain. Humanization can be essentially performed following the method of Winter and co-workers (Jones et al., *Nature,* 321, pp. 522 (1986); Riechmann et al., *Nature,* 332, pp. 323 (1988); Verhoeyen et al., *Science,* 239, pp. 1534 (1988)). Accordingly, such "humanized" antibodies are chimeric antibodies (Cabilly et al., U.S. Pat. No. 4,816,567), wherein substantially less than an intact human variable domain has been substituted by the corresponding sequence from the original antibody. In practice, humanized antibodies according to this invention are typically human antibodies in which some CDR residues and possibly some FR residues are substituted by residues from analogous sites in the original antibody.

The choice of human variable domains, both light and heavy, to be used in making the humanized antibodies is very important to reduce antigenicity. According to the so-called "best-fit" method, the sequence of the variable domain of an antibody of this invention is screened against the entire library of known human variable-domain sequences. The human sequence which is closest to that of the mouse is then accepted as the human framework (FR) for the humanized antibody (Sims et al., *J. Immunol.,* 151, pp. 2296 (1993); Chothia and Lesk, *J. Mol. Biol.,* 196, pp. 901 (1987)). Another method uses a particular framework from the consensus sequence of all human antibodies of a particular subgroup of light or heavy chains. The same framework can be used for several different humanized antibodies (Carter et al., *Proc. Natl. Acad. Sci. U.S.A.,* 89, pp. 4285 (1992); Presta et al., *J. Immunol.,* 51, pp. 1993)).

It is further important that antibodies be humanized with retention of high affinity for multiple inhibitory KIR receptors and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Another method of making "humanized" monoclonal antibodies is to use a XenoMouse® (Abgenix, Fremont, Calif.) as the mouse used for immunization. A XenoMouse is a murine host according to this invention that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference. An analogous method can be achieved using a HuMAb-Mouse™ (Medarex).

Human antibodies may also be produced according to various other techniques, such as by using, for immunization, other transgenic animals that have been engineered to express a human antibody repertoire (Jakobovitz et al., Nature 362 (1993) 255), or by selection of antibody repertoires using phage display methods. Such techniques are known to the skilled person and can be implemented starting from monoclonal antibodies as disclosed in the present application.

The antibodies of the present invention, preferably a DF-200-like antibody, may also be derivatized to "chimeric" antibodies (immunoglobulins) in which a portion of the heavy and/or light chain is identical with or homologous to corresponding sequences in the original antibody, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., *Proc. Natl. Acad. Sci. U.S.A.,* 81, pp. 6851 (1984)).

Other derivatives within the scope of this invention include functionalized antibodies, i.e., antibodies that are conjugated or covalently bound to a toxin, such as ricin, diphtheria toxin, abrin and *Pseudomonas* exotoxin; to a detectable moiety, such as a fluorescent moiety, a radioisotope or an imaging agent; or to a solid support, such as agarose beads or the like. Methods for conjugation or covalent bonding of these other agents to antibodies are well known in the art.

Conjugation to a toxin is useful for targeted killing of NK cells displaying one of the cross-reacting KIR receptors on its cell surface. Once the antibody of the invention binds to the cell surface of such cells, it is internalized and the toxin is released inside of the cell, selectively killing that cell. Such use is an alternate embodiment of the present invention.

Conjugation to a detectable moiety is useful when the antibody of this invention is used for diagnostic purposes. Such purposes include, but are not limited to, assaying biological samples for the presence of the NK cells bearing the cross-reacting KIR on their cell surface and detecting the presence of NK cells bearing the cross-reacting KIR in a living organism. Such assay and detection methods are also alternate embodiments of the present invention.

Conjugation of an antibody of this invention to a solid support is useful as a tool for affinity purification of NK cells bearing the cross-reacting KIR on their cell surface from a source, such as a biological fluid. This method of purification is another alternate embodiment of the present invention, as is the resulting purified population of NK cells.

In an alternate embodiment, an antibody that binds a common determinant present on at least two different human inhibitory KIR receptor gene products, wherein said antibody is capable of neutralizing KIR-mediated inhibition of NK cell cytotoxicity on NK cells expressing at least one of said two different human inhibitory KIR receptors of this invention, including NKVSF1, may be incorporated into liposomes ("immunoliposomes"), alone or together with another substance for targeted delivery to an animal. Such other substances include nucleic acids for the delivery of genes for gene therapy or for the delivery of antisense RNA, RNAi or siRNA for suppressing a gene in an NK cell, or toxins or drugs for the targeted killing of NK cells.

Computer modelling of the extra-cellular domains of KIR2DL1, -2 and -3 (KIR2DL1-3), based on their published crystal-structures (Maenaka et al. (1999), Fan et al. (2001), Boyington et al. (2000)), predicted the involvement of certain regions or KIR2DL1, -2 and -3 in the interaction between KIR2DL1 and the KIR2DL1-3-cross-reactive mouse monoclonal antibodies DF200 and NKVSF1. Thus, in one embodiment, the present invention provides antibodies that exclusively bind to KIR2DL1 within a region defined by the amino acid residues (105, 106, 107, 108, 109, 110, 111, 127, 129, 130, 131, 132, 133, 134, 135, 152, 153, 154, 155, 156, 157, 158, 159, 160, 161, 162, 163, 181, 192).

In another embodiment the invention provides antibodies that bind to KIR2DL1 and KIR2DL2/3 without interacting with amino acid residues outside the region defined by the residues (105, 106, 107, 108, 109, 110, 111, 127, 129, 130, 131, 132, 133, 134, 135, 152, 153, 154, 155, 156, 157, 158, 159, 160, 161, 162, 163, 181, 192).

In another embodiment, the invention provides antibodies that bind to KIR2DL1 and which does not bind to a mutant of KIR2DL1 in which R131 is Ala.

In another embodiment, the invention provides antibodies that bind to KIR2DL1 and which does not bind to a mutant of KIR2DL1 in which R157 is Ala.

In another embodiment, the invention provides antibodies that bind to KIR2DL1 and which does not bind to a mutant of KIR2DL1 in which R158 is Ala.

In another embodiment, the invention provides antibodies that bind to KIR2DL1 residues (131, 157, 158).

In another embodiment, the invention provides antibodies that bind to KIR2DS3(R131W), but not to wild type KIR2DS3.

In another embodiment, the invention provides antibodies that bind to both KIR2DL1 and KIR2DL2/3 as well as KIR2DS4.

In another embodiment, the invention provides antibodies that bind to both KIR2DL1 and KIR2DL2/3, but not to KIR2DS4.

Determination of whether an antibody binds within one of the epitope regions defined above can be carried out in ways known to the person skilled in the art. As one example of such mapping/characterization methods, an epitope region for an anti-KIR antibody may be determined by epitope "foot-printing" using chemical modification of the exposed amines/carboxyls in the KIR2DL1 or KIR2DL2/3 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from hack exchange and therefore will remain deuterated. Relevant regions can be identified at this point by peptic proteolysis, fast micropore high-performance liquid chromatography separation, and/or electrospray ionization mass spectrometry. See, e.g., Ehring H, Analytical Biochemistry, Vol. 267 (2) pp. 252-259 (1999) and/or Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectres of the free antigen and the antigen complexed with the antigen binding peptide, such as an antibody, are compared. The antigen typically is selectively isotopically labeled with $^{15}$N so that only signals corresponding to the antigen and no signals from the antigen binding peptide are seen in the NMR-spectrum. Antigen signals originating from amino acids involved in the interaction with the antigen binding peptide typically will shift position in the spectres of the complex compared to the spectres of the free antigen, and the amino acids involved in the binding can be identified that way. See, e.g., Ernst Schering Res Found Workshop. 2004; (44):149-67; Huang et al, Journal of Molecular Biology, Vol. 281 (1) pp. 61-67 (1998); and Saito and Patterson, Methods. 1996 June; 9(3):516-24.

Epitope mapping/characterization also can be performed using mass spectrometry methods. See, e.g., Downward, J Mass Spectrom. 2000 April; 35(4):493-503 and Kiselar and Downard, Anal Chem. 1999 May 1; 71(9):1792-801.

Protease digestion techniques also can be useful in the context of epitope mapping and identification. Antigenic determinant-relevant regions/sequences can be determined by protease digestion, e.g. by using trypsin in a ratio of about 1:50 to KIR2DL1 or KIR2DL2/3 o/n digestion at 37° C. and pH 7-8, followed by mass spectrometry (MS) analysis for peptide identification. The peptides protected from trypsin cleavage by the anti-KIR binder can subsequently be identified by comparison of samples subjected to trypsin digestion and samples incubated with antibody and then subjected to digestion by e.g. trypsin (thereby revealing a foot print for the binder). Other enzymes like chymotrypsin, pepsin, etc., also or alternatively can be used in a similar epitope characterization methods. Moreover, enzymatic digestion can provide a quick method for analyzing whether a potential antigenic determinant sequence is within a region of the KIR2DL1 in the context of a Anti-KIR polypeptide that is not surface exposed and, accordingly, most likely not relevant in terms of immunogenicity/antigenicity. See, e.g., Manca, Ann Ist Super Sanita. 1991; 27(1):15-9 for a discussion of similar techniques.

Crossreactivity with Cynomolgus Monkeys

It has been found that antibody NKVSF1 also binds to NK cells from cynomolgus monkeys, see example 7. The invention therefore provides an antibody, as well as fragments and derivatives thereof, wherein said antibody, fragment or derivative cross-reacts with at least two inhibitory human KIR receptors at the surface of human NK cells, and which furthermore binds to NK cells from cynomolgus monkeys. In one embodiment hereof, the antibody is not antibody NKVSF1. The invention also provides a method of testing the toxicity of an antibody, as well as fragments and derivatives thereof, wherein said antibody, fragment or derivative cross-reacts with at least two inhibitory human KIR receptors at the surface of human NK cells, wherein the method comprises testing the antibody in a cynomolgus monkey.

Compositions and Administration

The invention also provides pharmaceutical compositions that comprise an antibody, as well as fragments and derivatives thereof, wherein said antibody, fragment or derivative cross-reacts with at least two inhibitory KIR receptors at the surface of NK cells, neutralizes their inhibitory signals and potentiates the activity of those cells, in any suitable vehicle in an amount effective to detectably potentiate NK cell cytotoxicity in a patient or in a biological sample comprising NK cells. The composition further comprises a pharmaceutically acceptable carrier. Such compositions are also referred to as "antibody compositions of this invention." In one embodiment, antibody compositions of this invention comprise an antibody disclosed in the antibody embodiments above. The antibody NKVSF1 is included within the scope of antibodies that may be present in the antibody compositions of this invention.

The term "biological sample" as used herein includes but is not limited to a biological fluid (for example serum, lymph, blood), cell sample or tissue sample (for example bone marrow).

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of this invention may be employed in a method of potentiating the activity of NK cells in a patient or a biological sample. This method comprises the step of contacting said composition with said patient or biological sample. Such method will be useful for both diagnostic and therapeutic purposes.

For use in conjunction with a biological sample, the antibody composition can be administered by simply mixing with or applying directly to the sample, depending upon the nature of the sample (fluid or solid). The biological sample may be contacted directly with the antibody in any suitable device (plate, pouch, flask, etc.). For use in conjunction with a patient, the composition must be formulated for administration to the patient.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the compositions may be formulated in an ointment such as petrolatum.

The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Several monoclonal antibodies have been shown to be efficient in clinical situations, such as Rituxan (Rituximab), Herceptin (Trastuzumab) or Xolair (Omalizumab), and similar administration regimens (i.e., formulations and/or doses and/or administration protocols) may be used with the antibodies of this invention. Schedules and dosages for administration of the antibody in the pharmaceutical compositions of the present invention can be determined in accordance with known methods for these products, for example using the manufacturers' instructions. For example, an antibody present in a pharmaceutical composition of this invention can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 10 mg/m$^2$ and 500 mg/m$^2$. However, it will be appreciated that these schedules are exemplary and that an optimal schedule and regimen can be adapted taking into account the affinity and tolerability of the particular antibody in the pharmaceutical composition that must be determined in clinical trials. Quantities and schedule of injection of an antibody in a pharmaceutical composition of this invention that saturate NK cells for 24 hours, 48 hours 72 hours or a week or a month will be determined considering the affinity of the antibody and the its pharmacokinetic parameters.

According to another embodiment, the antibody compositions of this invention may further comprise another therapeutic agent, including agents normally utilized for the particular therapeutic purpose for which the antibody is being administered. The additional therapeutic agent will normally be present in the composition in amounts typically used for that agent in a monotherapy for the particular disease or condition being treated. Such therapeutic agents include, but are not limited to, therapeutic agents used in the treatment of cancers, therapeutic agents used to treat infectious disease, therapeutic agents used in other immunotherapies, cytokines (such as IL-2 or IL-15), other antibodies and fragments of other antibodies.

For example, a number of therapeutic agents are available for the treatment of cancers. The antibody compositions and methods of the present invention may be combined with any other methods generally employed in the treatment of the particular disease, particularly a tumor, cancer disease, or other disease or disorder that the patient exhibits. So long as a particular therapeutic approach is not known to be detrimental to the patient's condition in itself, and does not significantly counteract the activity of the antibody in a pharmaceutical composition of this invention, its combination with the present invention is contemplated.

In connection with solid tumor treatment, the pharmaceutical compositions of the present invention may be used in combination with classical approaches, such as surgery, radiotherapy, chemotherapy, and the like. The invention therefore provides combined therapies in which a pharmaceutical composition of this invention is used simultaneously with, before, or after surgery or radiation treatment; or are administered to patients with, before, or after conventional chemotherapeutic, radiotherapeutic or anti-angiogenic agents, or targeted immunotoxins or coaguligands.

When one or more agents are used in combination with an antibody-containing composition of this invention in a therapeutic regimen, there is no requirement for the combined results to be additive of the effects observed when each treatment is conducted separately. Although at least additive effects are generally desirable, any increased anti-cancer effect above one of the single therapies would be of benefit. Also, there is no particular requirement for the combined treatment to exhibit synergistic effects, although this is certainly possible and advantageous.

To practice combined anti-cancer therapy, one would simply administer to an animal an antibody composition of this invention in combination with another anti-cancer agent in a manner effective to result in their combined anti-cancer actions within the animal. The agents would therefore be provided in amounts effective and for periods of time effective to result in their combined presence within the tumor vasculature and their combined actions in the tumor environment. To achieve this goal, an antibody composition of this invention and anti-cancer agents may be administered to the animal simultaneously, either in a single combined composition, or as two distinct compositions using different administration routes.

Alternatively, the administration of an antibody composition of this invention may precede, or follow, the anti-cancer agent treatment by, e.g., intervals ranging from minutes to weeks and months. One would ensure that the anti-cancer agent and an antibody in the antibody composition of this invention exert an advantageously combined effect on the cancer.

Most anti-cancer agents would be given prior to an inhibitory KIR antibody composition of this invention in an anti-angiogenic therapy. However, when immunoconjugates of an antibody are used in the antibody composition of this invention, various anti-cancer agents may be simultaneously or subsequently administered.

In some situations, it may even be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administration of the anti-cancer agent or anti-cancer treatment and the administration of an antibody composition of this invention. This would be advantageous in circumstances where the anti-cancer treatment was intended to substantially destroy the tumor, such as surgery or chemotherapy, and administration of an antibody composition of this invention was intended to prevent micrometastasis or tumor re-growth.

It also is envisioned that more than one administration of either an inhibitory KIR antibody-based composition of this invention or the anti-cancer agent will be utilized. These agents may be administered interchangeably, on alternate days or weeks; or a cycle of treatment with an inhibitory KIR antibody composition of this invention, followed by a cycle of anti-cancer agent therapy. In any event, to achieve tumor regression using a combined therapy, all that is required is to deliver both agents in a combined amount effective to exert an anti-tumor effect, irrespective of the times for administration.

In terms of surgery, any surgical intervention may be practiced in combination with the present invention. In connection with radiotherapy, any mechanism for inducing DNA damage locally within cancer cells is contemplated, such as gamma-irradiation, X-rays, UV-irradiation, microwaves and even electronic emissions and the like. The directed delivery of radioisotopes to cancer cells is also contemplated, and this may be used in connection with a targeting antibody or other targeting means.

In other aspects, immunomodulatory compounds or regimens may be administered in combination with or as part of the antibody compositions of the present invention. Preferred examples of immunomodulatory compounds include cytokines. Various cytokines may be employed in such combined approaches. Examples of cytokines useful in the combinations contemplated by this invention include IL-1alpha IL-1beta, IL-2, IL-3, IL-4, IL-5, IL-6, IL-7, IL-8, IL-9, IL-10, IL-11, IL-12, IL-13, IL-15, IL-21, TGF-beta, GM-CSF, M-CSF, G-CSF, TNF-alpha, TNF-beta, LAF, TCGF, BCGF, TRF, BAF, BDG, MP, LIF, OSM, TMF, PDGF, IFN-alpha, IFN-beta, IFN-gamma. Cytokines used in the combination treatment or compositions of this invention are administered according to standard regimens, consistent with clinical indications such as the condition of the patient and relative toxicity of the cytokine.

In certain embodiments, the cross-reacting inhibitory KIR antibody-comprising therapeutic compositions of the present invention may be administered in combination with or may further comprise a chemotherapeutic or hormonal therapy agent. A variety of hormonal therapy and chemotherapeutic agents may be used in the combined treatment methods disclosed herein. Chemotherapeutic agents contemplated as exemplary include, but are not limited to, alkylating agents, antimetabolites, cytotoxic antibiotics, vinca alkaloids, for example adriamycin, dactinomycin, mitomycin, carminomycin, daunomycin, doxorubicin, tamoxifen, taxol, taxotere, vincristine, vinblastine, vinorelbine, etoposide (VP-16), 5-fluorouracil (5FU), cytosine arabinoside, cyclophosphamide, thiotepa, methotrexate, camptothecin, actinomycin-D, mitomycin C, cisplatin (CDDP), aminopterin, combretastatin(s) and derivatives and prodrugs thereof.

Hormonal agents include, but are not limited to, for example LHRH agonists such as leuprorelin, goserelin, triptorelin, and buserelin; anti-estrogens such as tamoxifen and toremifene; anti-androgens such as flutamide, nilutamide, cyproterone and bicalutamide; aromatase inhibitors such as anastrozole, exemestane, letrozole and fadrozole; and progestagens such as medroxy, chlormadinone and megestrol.

As will be understood by those of ordinary skill in the art, the appropriate doses of chemotherapeutic agents will approximate those already employed in clinical therapies wherein the chemotherapeutics are administered alone or in combination with other chemotherapeutics. By way of example only, agents such as cisplatin, and other DNA alkylating may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Further useful chemotherapeutic agents include compounds that interfere with DNA replication, mitosis and chromosomal segregation, and agents that disrupt the synthesis and fidelity of polynucleotide precursors. A number of exemplary chemotherapeutic agents for combined therapy are listed in Table C of U.S. Pat. No. 6,524,583, the disclosure of which agents and indications are specifically incorporated herein by reference. Each of the agents listed are exemplary and not limiting. The skilled artisan is directed to "Remington's Pharmaceutical Sciences" 15th Edition, chapter 33, in particular pages 624-652. Variation in dosage will likely occur depending on the condition being treated. The physician administering treatment will be able to determine the appropriate dose for the individual subject.

The present cross-reacting inhibitory KIR antibody compositions of this invention may be used in combination with any one or more other anti-angiogenic therapies or may further comprise anti-angiogenic agents. Examples of such agents include neutralizing antibodies, antisense RNA, siRNA, RNAi, RNA aptamers and ribozymes each directed against VEGF or VEGF receptors (U.S. Pat. No. 6,524,583, the disclosure of which is incorporated herein by reference). Variants of VEGF with antagonistic properties may also be employed, as described in WO 98/16551, specifically incorporated herein by reference. Further exemplary anti-angiogenic agents that are useful in connection with combined therapy are listed in Table D of U.S. Pat. No. 6,524,583, the disclosure of which agents and indications are specifically incorporated herein by reference.

The inhibitory KIR antibody compositions of this invention may also be advantageously used in combination with methods to induce apoptosis or may comprise apoptotic agents. For example, a number of oncogenes have been identified that inhibit apoptosis, or programmed cell death. Exemplary oncogenes in this category include, but are not limited to, bcr-abl, bcl-2 (distinct from bcl-1, cyclin D1; GenBank accession numbers M14745, X06487; U.S. Pat. Nos. 5,650,491; and 5,539,094; each incorporated herein by reference) and family members including Bcl-x1, Mcl-1, Bak, A1, and A20. Overexpression of bcl-2 was first discovered in T cell lymphomas. The oncogene bcl-2 functions by binding and inactivating Bax, a protein in the apoptotic pathway. Inhibition of bcl-2 function prevents inactivation of Bax, and allows the apoptotic pathway to proceed. Inhibition of this class of oncogenes, e.g., using antisense nucleotide sequences, RNAi, siRNA or small molecule chemical compounds, is contemplated for use in the present invention to give enhancement of apoptosis (U.S. Pat. Nos. 5,650,491; 5,539,094; and 5,583,034; each incorporated herein by reference).

The inhibitory KIR antibody compositions of this invention may also comprise or be used in combination with molecules that comprise a targeting portion, e.g., antibody, ligand, or conjugate thereof, directed to a specific marker of a target cell ("targeting agent"), for example a target tumor cell. Generally speaking, targeting agents for use in these additional aspects of the invention will preferably recognize accessible tumor antigens that are preferentially, or specifically, expressed in the tumor site. The targeting agents will generally bind to a surface-expressed, surface-accessible or surface-localized component of a tumor cell. The targeting agents will also preferably exhibit properties of high affinity; and will not exert significant in vivo side effects against life-sustaining normal tissues, such as one or more tissues selected from heart, kidney, brain, liver, bone marrow, colon, breast, prostate, thyroid, gall bladder, lung, adrenals, muscle, nerve fibers, pancreas, skin, or other life-sustaining organ or tissue in the human body. The term "not exert significant side effects," as used herein, refers to the fact that a targeting agent, when administered in vivo, will produce only negligible or clinically manageable side effects, such as those normally encountered during chemotherapy.

In the treatment of tumors, an antibody composition of this invention may additionally comprise or may be used in combination with adjunct compounds. Adjunct compounds may include by way of example anti-emetics such as serotonin antagonists and therapies such as phenothiazines, substituted benzamides, antihistamines, butyrophenones, corticosteroids, benzodiazepines and cannabinoids; bisphosphonates such as zoledronic acid and pamidronic acid; and hematopoietic growth factors such as erythropoietin and G-CSF, for example filgrastim, lenograstim and darbepoietin.

In another embodiment, two or more antibodies of this invention having different cross-reactivities, including NKVSF1, may be combined in a single composition so as to neutralize the inhibitory effects of as many inhibitory KIR gene products as possible. Compositions comprising combinations of cross-reactive inhibitory KIR antibodies of this invention, or fragments or derivatives thereof, will allow even wider utility because there likely exists a small percentage of the human population that may lack each of the inhibitory KIR gene products recognized by a single cross-reacting antibody. Similarly, an antibody composition of this invention may further comprise one or more antibodies that recognize single inhibitory KIR subtypes. Such combinations would again provide wider utility in a therapeutic setting.

The invention also provides a method of potentiating NK cell activity in a patient in need thereof, comprising the step of administering a composition according to this invention to said patient. The method is more specifically directed at increasing NK cell activity in patients having a disease in which increased NK cell activity is beneficial, which involves, affects or is caused by cells susceptible to lysis by NK cells, or which is caused by or characterized by insufficient NK cell activity, such as a cancer, another proliferative disorder, an infectious disease or an immune disorder. More specifically, the methods of the present invention are utilized for the treatment of a variety of cancers and other proliferative diseases including, but not limited to, carcinoma, including that of the bladder, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma.

Preferred disorders that can be treated according to the invention include hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; Sezary syndrome (SS); Adult T-cell leukemia lymphoma (ATLL); a/d T-NHL hepatosplenic lymphoma; peripheral/post-thymic T cell lymphoma (pleomorphic and immunoblastic subtypes); angio immunoblastic T-cell lymphoma; angiocentric (nasal) T-cell lymphoma; anaplastic (Ki 1+) large cell lymphoma; intestinal T-cell lymphoma; T-lymphoblastic; and lymphoma/leukaemia (T-Lbly/T-ALL).

Other proliferative disorders can also be treated according to the invention, including for example hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

The cross-reacting inhibitory KIR antibody of this invention can be used to treat or prevent infectious diseases, including preferably any infections caused by viruses, bacteria, protozoa, molds or fungi. Such viral infectious organisms include, but are not limited to, hepatitis type A, hepatitis type B, hepatitis type C, influenza, varicella, adenovirus, herpes simplex type I (HSV-1), herpes simplex type 2 (HSV-2), rinderpest, rhinovirus, echovirus, rotavirus, respiratory syncytial virus, papilloma virus, papilloma virus, cytomegalovirus, echinovirus, arbovirus, huntavirus, coxsackie virus, mumps virus, measles virus, rubella virus, polio virus and human immunodeficiency virus type I or type 2 (HIV-1, HIV-2).

Bacterial infections that can be treated according to this invention include, but are not limited to, infections caused by the following: *Staphylococcus; Streptococcus*, including *S. pyogenes; Enterococcl; Bacillus*, including *Bacillus anthracis*, and *Lactobacillus; Listeria; Corynebacterium diphtheriae; Gardnerella* including *G. vaginalis; Nocardia; Streptomyces; Thermoactinomyces vulgaris; Treponema; Camplyobacter, Pseudomonas* including Raeruginosa; *Legionella; Neisseria* including *N. gonorrhoeae* and *N. meningitides; Flavobacterium* including *F. meningosepticum* and *F. odoraturn; Brucella; Bordetella* including *B. pertussis* and *B. bronchiseptica; Escherichia* including *E. coli, Klebsiella; Enterobacter, Serratia* including *S. marcescens* and *S. liquefaciens; Edwardsiella; Proteus* including *P. mirabilis* and *P. vulgaris; Streptobacillus*; Rickettsiaceae including *R. fickettsfi, Chlamydia* including *C. psittaci* and *C. trachornatis; Mycobacterium* including *M. tuberculosis, M. intracellulare, M. folluiturn, M. laprae, M. avium, M. bovis, M. africanum, M. kansasii, M. intracellulare*, and *M. lepraernurium*; and *Nocardia*.

Protozoa infections that may be treated according to this invention include, but are not limited to, infections caused by *leishmania, kokzidioa*, and *trypanosoma*. A complete list of infectious diseases can be found on the website of the National Center for Infectious Disease (NCID) at the Center for Disease Control (CDC) (http://www.cdc.gov/ncidod/diseases/), which list is incorporated herein by reference. All of said diseases are candidates for treatment using the cross-reacting inhibitory KIR antibodies of the invention.

Such methods of treating various infectious diseases may employ the antibody composition of this invention, either alone or in combination with other treatments and/or therapeutic agents known for treating such diseases, including anti-viral agents, anti-fungal agents, antibacterial agents, antibiotics, anti-parasitic agents and anti-protozoal agents. When these methods involve additional treatments with additional therapeutic agents, those agents may be administered together with the antibodies of this invention as either a single dosage form or as separate, multiple dosage forms. When administered as a separate dosage form, the additional agent may be administered prior to, simultaneously with, of following administration of the antibody of this invention.

Further aspects and advantages of this invention will be disclosed in the following experimental section, which should be regarded as illustrative and not limiting the scope of this application.

Example 1

Purification of PBLs and Generation of Polyclonal or Clonal NK Cell Lines

PBLs were derived from healthy donors by Ficoll Hypaque gradients and depletion of plastic adherent cells. To obtain enriched NK cells, PBLs were incubated with anti CD3, anti CD4 and anti HLA-DR mAbs (30 minutes at 4° C.), followed by goat anti mouse magnetic beads (Dynal) (30 minutes at 4° C.) and immunomagnetic selection by methods known in the art (Pende et al., 1999). CD3$^-$, CD4$^-$, DR$^-$ cells were cultivated on irradiated feeder cells and 100 U/ml Interleukin 2 (Proleukin, Chiron Corporation) and 1.5 ng/ml Phytohemagglutinin A (Gibco BRL) to obtain polyclonal NK cell populations. NK cells were cloned by limiting dilution and clones of NK cells were characterized by flow cytometry for expression of cell surface receptors.

The mAbs used were JT3A (IgG2a, anti CD3), EB6 and GL183 (IgG1 anti KIR2DL1 and KIR2DL3 respectively), XA-141 IgM (anti KIR2DL1 with the same specificity as EB6), anti CD4 (HP2.6), and anti DR (D1.12, IgG2a). Instead of JT3A, HP2.6, and DR1.12, which were produced by applicants, commercially available mAbs of the same specificities can be used (Beckman Coulter Inc., Fullerton, Calif.). EB6 and GL183 are commercially available (Beckman Coulter Inc., Fullerton, Calif. XA-141 is not commercially available, but EB6 can be used for control reconstitution of lysis as described in (Moretta et al., 1993).

Cells were stained with the appropriate antibodies (30 mns at 4° C.) followed by PE or FITC conjugated polyclonal anti mouse antibodies (Southern Biotechnology Associates Inc). Samples were analyzed by cytofluorometric analysis on a FACSAN apparatus (Becton Dickinson, Mountain View, Calif.).

The following clones were used in this study. CP11, CN5 and CN505 are KIR2DL1 positive clones and are stained by EB6 ((IgG1 anti KIR2DL1) or XA-141 (IgM anti KIR2DL1 with same specificity as compared to EB6 antibodies). CN12 and CP502 are KIR2DL3 positive clones and are stained by GL183 antibody (IgG1 anti KIR2DL3).

The cytolytic activity of NK clones was assessed by a standard 4 hour $^{51}$Cr release assay in which effector NK cells were tested on Cw3 or Cw4 positive cell lines known for their sensitivity to NK cell lysis. All the targets were used at 5000 cells per well in microtitration plate and the effector: target ratio is indicated in the Figures (usually 4 effectors per target cells). The cytolytic assay was performed with or without supernatant of the indicated monoclonal antibodies at a ½ dilution. The procedure was essentially the same as described in (Moretta et al., 1993).

Example 2

Generation of New mAbs mAbs were generated by immunizing 5 week old Balb C mice with activated polyclonal or monoclonal NK cell lines as described in (Moretta et al., 1990). After different cell fusions, the mAbs were first selected for their ability to cross-react with EB6 and GL183 positive NK cell lines and clones. Positive monoclonal antibodies were further screened for their ability to reconstitute lysis by EB6 positive or GL183 positive NK clones of Cw4 or Cw3 positive targets respectively.

Cell staining was carried out as follows. Cells were stained with a panel of antibodies (1 µg/ml or 50 µl supernatant, 30 mns at 4° C.) followed by PE-conjugated goat F(ab')2 fragments anti-mouse IgG (H+L) or PE-conjugated goat F(ab')2 fragment anti-human IgG (Fc gamma) antibodies (Beckman Coulter). Cytofluorometric analysis was performed on an Epics XL.MCL apparatus (Beckman Coulter).

One of the monoclonal antibodies, the DF200 mAb, was found to react with various members of the KIR family including KIR2DL1, KIR2DL2/3. Both KIR2DL1+ and KIR2DL2/3+ NK cells were stained brightly with DF200mAb (FIG. 1).

NK clones expressing one or another (or even both) of these HLA class I-specific inhibitory receptors were used as effectors cells against target cells expressing one or more HLA-C alleles. Cytotoxicity assays were carried out as follows. The cytolytic activity of YTS-KIR2DL1 or YTS-Eco cell lines was assessed by a standard 4 hours 51Cr release assay. The effector cells were tested on HLA-Cw4 positive or negative EBV cell lines and HLA-Cw4 transfected 721.221 cells. All targets were used at 3000 cells per well in microtitration plate. The effector/target ratio is indicated in the figures. The cytolytic assay was performed with or without the indicated full length or F(ab')2 fragments of monoclonal mouse or human antibodies. As expected, KIR2DL1$^+$ NK clones displayed little if any cytolytic activity against target cells expressing HLA-Cw4 and KIR2DL3$^+$ NK clones displayed little or no activity on Cw3 positive targets. However, in the presence of DF200mAb (used to mask their KIR2DL receptors) NK clones became unable to recognize their HLA-C ligands and displayed strong cytolytic activity on Cw3 or Cw4 targets.

Figure 2:
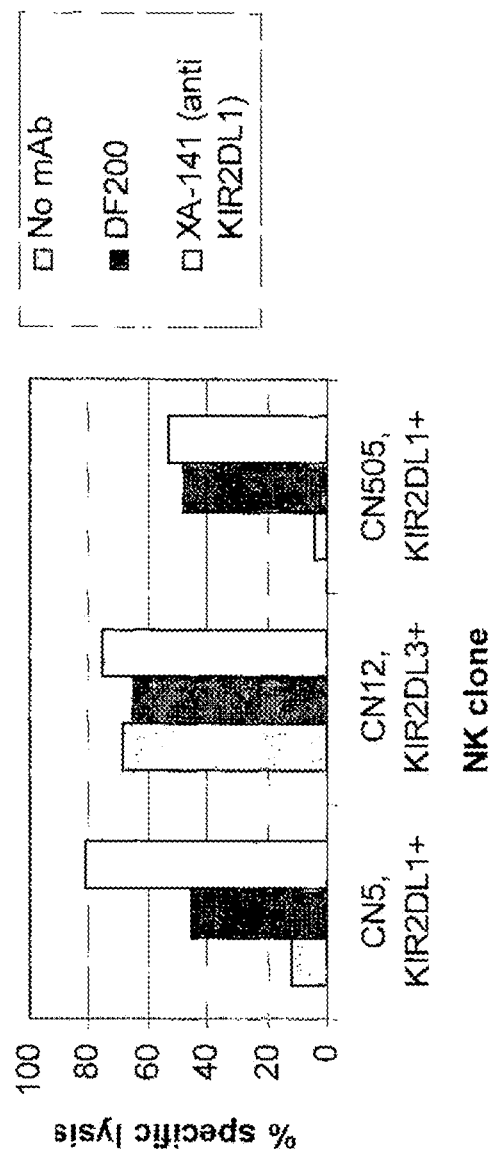
FIG. 2 depicts monoclonal antibody DF200 neutralizing the KIR2DL-mediated inhibition of KIR2DL1 positive NK cell cytotoxicity on Cw4 positive target cells.

For example, the C1R cell line (CW4$^+$ EBV cell line, ATCC n°CRL 1993) was not killed by KIR2DL1$^+$ NK clones (CN5/CN505), but the inhibition could be efficiently reversed by the use of either DF200 or a conventional anti KIR2DL1 mAb. On the other hand NK clones expressing the KIR2DL2/3$^+$ KIR2DL1$^-$ phenotype (CN12) efficiently killed C1R cells and this killing was unaffected by the DF200mAb (FIG. 2). Similar results are obtained with KIR2DL2- or KIR2DL3-positive NK clones on Cw3 positive targets.

Figure 3:
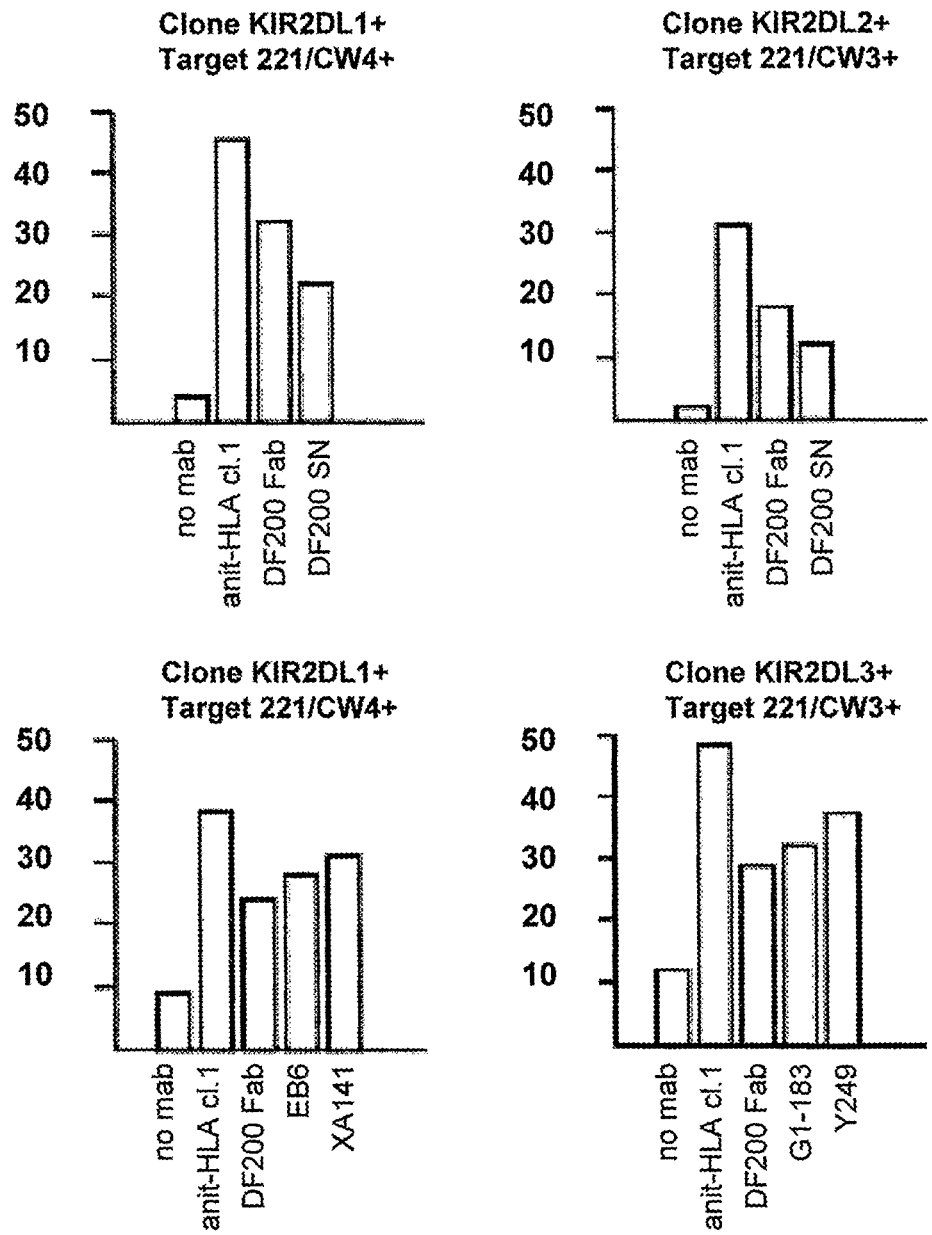
FIG. 3 depicts monoclonal antibody DF200, a Fab fragment of DF200 and KIR2DL1 or KIR2DL2/3 specific conventional antibodies neutralizing the KIR2DL-mediated inhibition of KIR2DL1 positive NK cell cytotoxicity on Cw4 positive target cells and the KIR2DL-mediated inhibition of KIR2DL2/3 positive NK cell cytotoxicity on Cw3 positive target cells.

Similarly, the Cw4+ 221 EBV cell line was not killed by KIR2DL1$^+$ transfected NK cells, but the inhibition could be efficiently reversed by the use of either DF200, a DF200 Fab fragment, or a conventional anti KIR2DL1 mAb EB6 or XA141. Also, a Cw3+ 221 EBV cell line was not killed by KIR2DL2$^+$ NK cells, but this inhibition could be reversed by the use of either DF200 or a DF200 Fab fragment. Finally, the latter Cw3+ 221 EBV cell line was not killed by KIR2DL3$^+$ NK cells, but this inhibition could be reversed by the use of either a DF200 Fab fragment or a conventional anti KIR2DL3 mAb GL183 or Y249. The results are shown in FIG. 3.

F(ab')2 fragments were also tested for their ability to reconstitute lysis of Cw4 positive targets. F(ab')2 fragments of the DF200 and EB6 Abs were both able to reverse inhibition of lysis by KIR2DL1-transfected NK cells of the Cw4 transfected 221 cell line and the Cw4+ TUBO EBV cell line. Results are shown in FIG. 4.

Example 4

Generation of New Human mAbs

Human monoclonal anti-KIR Abs were generated by immunizing transgenic mice engineered to express a human antibody repertoire with recombinant KIR protein. After different cell fusions, the mAbs were first selected for their ability to cross-react with immobilized KIR2DL1 and KIR2DL2 protein. Several monoclonal antibodies, including 1-7F9, 1-4F1, 1-6F5 and 1-6F1, were found to react with KIR2DL1 and KIR2DL2/3.

Positive monoclonal antibodies wore further screened for their ability to reconstitute lysis by EB6 positive NK transfectants expressing KIR2DL1 of Cw4-positive target cells. The NK cells expressing the HLA class 1-specific inhibitory receptors were used as effectors cells against target cells expressing one or more HLA-C alleles (FIGS. 5 and 6). Cytotoxicity assays were carried out as described above. The effector/target ratio is indicated in the Figures, and antibodies were used at either 10 ug/ml or 30 ug/ml.

As expected, KIR2DL1$^+$ NK cells displayed little if any cytolytic activity against target cells expressing HLA-Cw4. However, in the presence of 1-7F9 mAb, NK cells became unable to recognize their HLA-C ligands and displayed strong cytolytic activity on the Cw4 targets. For example, the two cell lines tested (the HLA-Cw4 transfected 721.221 and the CW4$^+$ EBV cell lines) were not killed by KIR2DL1$^+$ NK cells, but the inhibition could be efficiently reversed by the use of either Mab 1-7F9 or a conventional anti KIR2DL1 mAb EB6. Abs DF200 and panKIR (also referred to as NKVSF1) were compared to 1-7F9. Antibodies 1-4F1, 1-6F5 and 1-6F1 on the other hand were not able to reconstitute cell lysis by NK cells on Cw4 positive targets.

Example 5

Biacore Analysis of DF200 mAb/KIR2DL1 and DF200 mAb/KIR2DL3 Interactions

Production and Purification of Recombinant Proteins

The KIR2DL1 and KIR2DL3 recombinant proteins were produced in E. coli. cDNA encoding the entire extracellular domain of KIR2DL1 and KIR2DL3 were amplified by PCR from pCDM8 clone 47.11 vector (Biassoni et al, 1993) and RSVS(gpt)183 clone 6 vector (Wagtman et al, 1995) respectively, using the following primers:

Sense:
5'-GGAATTCCAGGAGGAATTTAAAATGCATGAGGGAGTCCACAG-3'

Anti-sense:
5'-CGGGATCCCAGGTGTCTGGGGTTACC-3'

They were cloned into the pML1 expression vector in frame with a sequence encoding a biotinylation signal (Saulquin et al, 2003).

Protein expression was performed in the BL21(DE3) bacterial strain (Invitrogen). Transfected bacteria were grown to $OD_{600}$=0.6 at 37° C. in medium supplemented with ampicillin (100 µg/ml) and expression was induced with 1 mM IPTG.

Proteins were recovered from inclusion bodies under denaturing conditions (8 M urea). Refolding of the recombinant proteins was performed in 20 mM Tris, pH 7.8, NaCl 150 mM buffer containing L-arginine (400 mM, Sigma) and β-mercaptoethanol (1 mM), at room temperature, by decreasing the urea concentration in a six step dialysis (4, 3, 2, 1 0.5 and 0 M urea, respectively). Reduced and oxidized glutathione (5 mM and 0.5 mM respectively, Sigma) were added during the 0.5 and 0 M urea dialysis steps. Finally, the proteins were dialyzed extensively against 10 mM Tris, pH 7.5, NaCl 150 mM buffer. Soluble, refolded proteins were concentrated and then purified on a Superdex 200 size-exclusion column (Pharmacia; AKTA system).

Surface plasmon resonance measurements were performed on a Biacore apparatus (Biacore). In all Biacore experiments HBS buffer supplemented with 0.05% surfactant P20 served as running buffer.

Protein Immobilisation.

Recombinant KIR2DL1 and KIR2DL3 proteins produced as described above were immobilized covalently to carboxyl groups in the dextran layer on a Sensor Chip CM5 (Biacore). The sensor chip surface was activated with EDC/NHS (N-ethyl-N'-(3-dimethylaminopropyl)carbodiimidehydrochloride and N-hydroxysuccinimide, Biacore). Proteins, in coupling buffer (10 mM acetate, pH 4.5) were injected. Deactivation of the remaining activated groups was performed using 100 mM ethanolamine pH 8 (Biacore).

Affinity Measurements.

For kinetic measurements, various concentrations of the soluble antibody ($1\times10^{-7}$ to $4\times10^{-10}$ M) were applied onto the immobilized sample. Measurements were performed at a 20 µl/min continuous flow rate. For each cycle, the surface of the sensor chip was regenerated by 5 µl injection of 10 mM NaOH pH 11. The BIAlogue Kinetics Evaluation program (BIAevaluation 3.1, Biacore) was used for data analysis. The soluble analyte (40 µl at various concentrations) was injected at a flow rate of 20 µl/min in HBS buffer, on dextran layers containing 500 or 540 reflectance units (RU), and 1000 or 700 RU of KIR2DL1 and KIR2DL3, respectively. Data are representative of 6 independent experiments. The results are shown in Table 1, below.

TABLE 1

BIAcore analysis of DF200 mAb binding to immobilized KIR2DL1 and KIR2DL3.

| Protein | $K_D$ ($10^{-9}$M) |
|---|---|
| KIR2DL1 | 10.9 +/− 3.8 |
| KIR2DL3 | 2.0 +/− 1.9 |

$K_D$: Dissociation constant.

Example 6

Biacore Competitive Binding Analysis of Marine and Human Anti-KIR Antibodies

Epitope mapping analysis was performed on immobilized KIR2DL1 (900 RU), KIR2DL3 (2000 RU) and KIR2 DS1 (1000 RU) with mouse anti-KIR 2D antibodies DF200, Pan2D, gl183 and EB6, and human anti-KIR2 D antibodies 1-4F1, 1-6F1, 1-6F5 and 1-7F9 as described previously (Gauthier et al 1999, Saunal and van Regenmortel 1995).

All experiments were done at a flow rate of 5 μl/min in HBS buffer with 2 min injection of the different antibodies at 15 μg/ml. For each couple of antibodies competitive binding analysis was performed in two steps. In the first step the first monoclonal antibody (mAb) was injected on KIR 2D target protein followed by the second mAb (without removing the first mAb) and second mAb RU value (RU2) was monitored. In the second step the second mAb was injected first, directly on nude KIR 2D protein, and mAb RU value (RU1) was monitored. Percent inhibition of second mAb binding to KIR 2D protein by first mab was calculated by: 100*(1−RU2/RU1).

Figure 7:
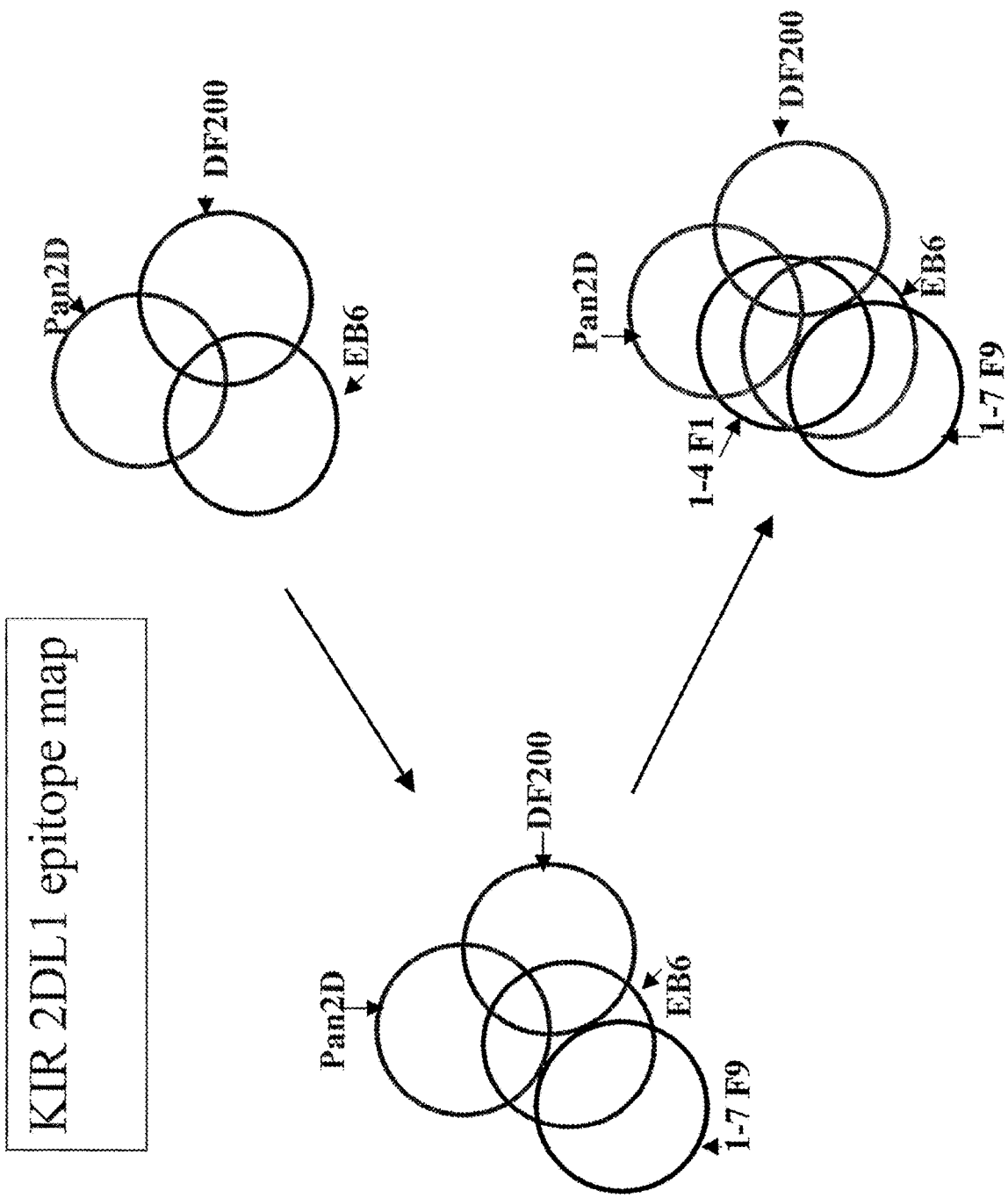
FIG. 7 depicts an epitope map showing results of competitive binding experiments obtained by surface plasmon resonance (BIAcore®) analysis with anti-KIR antibodies to KIR2DL1, where overlapping circles designate overlap in binding to KIR 2DL1. Results show that 1-7F9 is competitive with EB6 and 1-4F1, but not with NKVSF1 and DF200, on KIR 2DL1. Antibody 1-4F1 in turn is competitive with EB6, DF200, NKVSF1, and 1-7F9. Antibody NKVSF1 competes with DF200, 1-4F1, and EB6, but not 1-7F9, on KIR2DL1. DF200 competes with NKVSF1, 1-4F1, and EB6, but not 1-7F9, on KIR2DL1.
Figure 8:
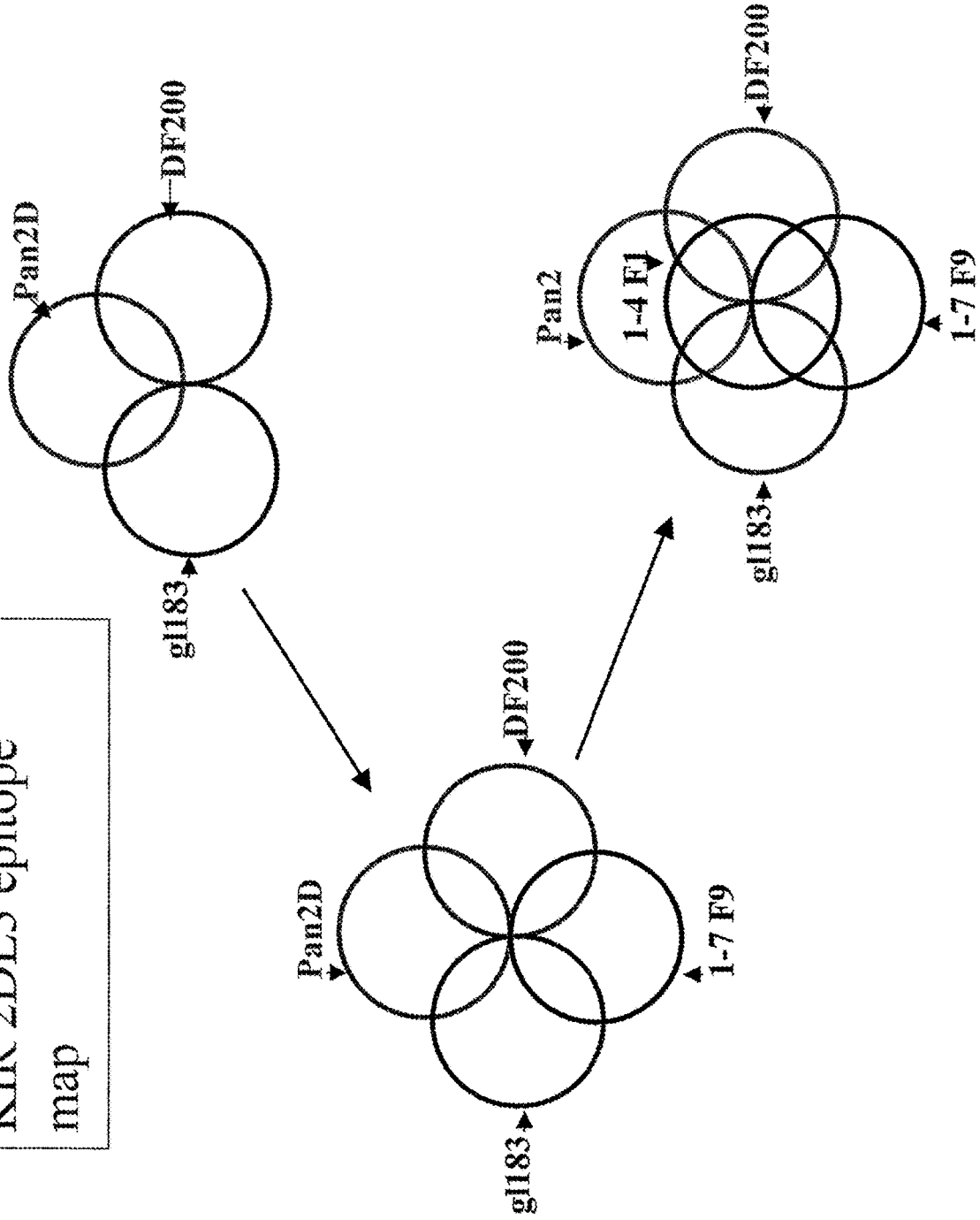
FIG. 8 depicts an epitope map showing results of competitive binding experiments obtained by BIAcore® analysis with anti-KIR antibodies to KIR2DL3, where overlapping circles designate overlap in binding to KIR2DL3. Results show that 1-4F1 is competitive with NKVSF1, DF200, gl183, and 1-7F9 on KIR2DL3. 1-7F9 is competitive with DF200, gl183, and 1-4F1, but not with NKVSF1, on KIR2DL3. NKVSF1 competes with DF200, 1-4F1, and GL183, but not 1-7F9, on KIR2DL3. DF200 competes with NKVSF1, 1-4F1, and 1-7F9, but not with GL183, on KIR2DL3.
Figure 9:
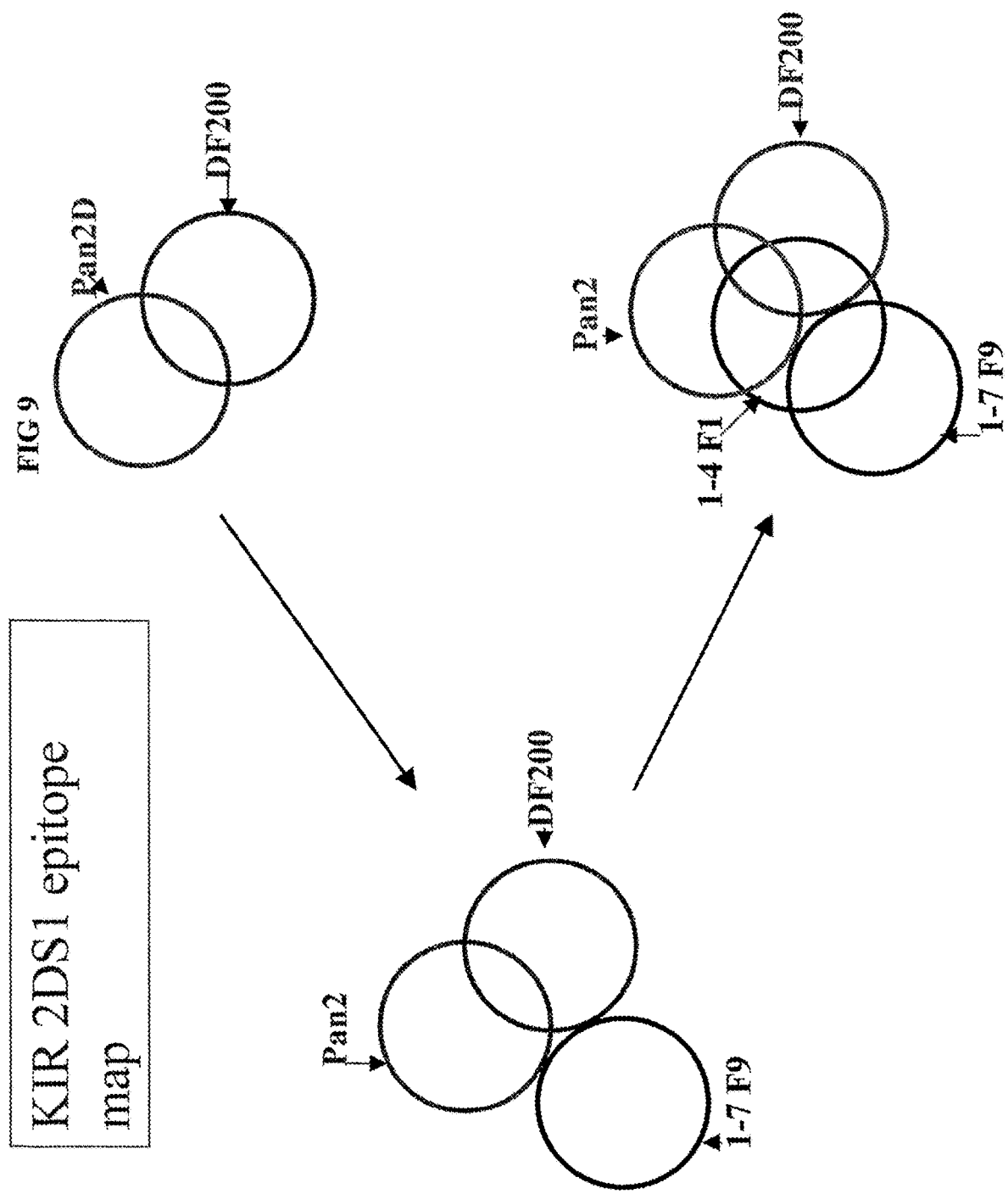
FIG. 9 depicts an epitope map showing results of competitive binding experiments obtained by BIAcore® analysis with anti-KIR antibodies to KIR2DS1, where overlapping circles designate overlap in binding to KIR2DS1. Results show that antibody 1-4F1 is competitive with NKVSF1, DF200, and 1-7F9 on KIR2DS1. Antibody 1-7F9 is competitive with 1-4F1, but not competitive with DF200 and NKVSF1 on KIR2DS1. NKVSF1 competes with DF200 and 1-4F1, but not with 1-7F9, on KIR2DS1, 200 competes with NKVSRF1 and 1-4F1, but not with 1-7F9, on KIR2DS1.

Results are shown in Tables 2, 3 and 4, where the antibodies designated 'first antibody' are listed on vertical column and the 'second antibody' are listed on the horizontal column. For each antibody combination tested, the values for direct binding level (RU) of the antibodies to the chip are listed in the table, where direct binding of the second antibody to the KIR2D chip is listed in the upper portion of the field and the value for binding of the second antibody to the KIR2D chip when the first antibody is present is listed in the lower portion of the field. Listed in the right of each field is the percentage inhibition of second antibody binding. Table 2 shows binding on a KIR2DL1 chip, Table 3 shows binding of antibodies to a KIR2DL3 chip, and Table 4 shows binding of antibodies to a KIR2DS1 chip. Competitive binding of murine antibodies DF200, NKVSF1 and EB6, and human antibodies 1-4F1, 1-7F9 and 1-6F1 to immobilized KIR2DL1, KIR2DL2/3 and KIR2DS1 was assessed. Epitope mapping (FIG. 7) from experiments with anti-KIR antibodies' binding to KIR2DL1 showed that (a) antibody 1-7F9 is competitive with EB6 and 1-4F1, but not with NKVSF1 and DF200; (b) antibody 1-4 F1 in turn is competitive with EB6, DF200, NKVSF1 and 1-7 F9; (c) NKVSF1 competes with DF200, 1-4F1 and EB6, but not 1-7F9; and (d) DF200 competes with NKVSF1, 1-4F1 and EB6, but not 1-7F9. Epitope mapping (FIG. 8) from experiments with anti-KIR antibodies' binding to KIR2DL3 showed that (a) 1-4F1 is competitive with NKVSF1, DF200, gl183 and 1-7F9; (b) 1-7F9 is competitive with DF200, gl183 and 1-4F1, but not with NKVSF1; (c) NKVSF1 competes with DF200, 1-4F1 and GL183, but not 1-7F9; and (d) DF200 competes with NKVSF1, 1-4F1 and 1-7F9, but not with GL183. Epitope mapping (FIG. 9) from experiments with anti-KIR antibodies' binding to KIR2DS1 showed that (a) 1-4F1 is competitive with NKVSF1, DF200 and 1-7F9; (b) 1-7F9 is competitive with 1-4F1 but not competitive with DF200 and NKVSF1; (c) NKVSF1 competes with DF200 and 1-4F1, but not 1-7F9; and (d) DF200 competes with NKVSF1 and 1-4F1, but not with 1-7F9.

Example 7

Anti-KIR mAb Titration with Cynomolgus NK Cells

Figure 10:
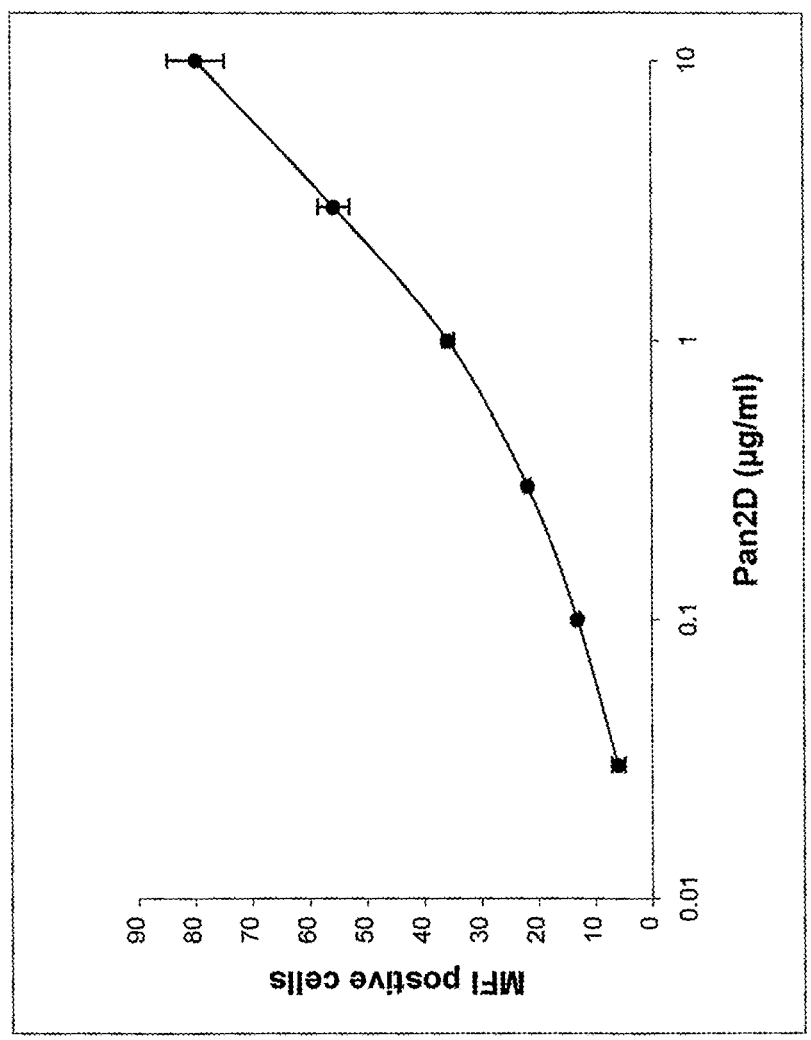
FIG. 10 depicts NKVSF1 (pan2D) mAb titration demonstrating binding of the mAb to cynomolgus NK cells. Cynomolgus NK cells (NK bulk day 16) were incubated with different amount of Pan2D mAb followed by PE-conjugated goat F(ab')2 fragments anti-mouse IgG (H+L) antibodies. The percentage of positive cells was determined with an isotypic control (purified mouse IgG1). Samples were done in duplicate. Mean fluorescence intensity=MFI.

Anti-KIR antibody NKVSF1 was tested for its ability to bind to NK cells from cynomolgus monkeys. Binding of the antibody to monkey NK cells is shown in FIG. 10.

Purification of Monkey PBMC and Generation of Polyclonal NK Cell Bulk.

Cynomolgus Macaque PBMC were prepared from Sodium citrate CPT tube (Becton Dickinson). NK cells purification was performed by negative depletion (Macaque NK cell enrichment kit, Stem Cell Technology). NK cells were cultivated on irradiated human feeder cells, 300 U/ml Interleukin 2 (Proleukin, Chiron Corporation) and 1 ng/ml Phytohemagglutinin A (Invitrogen, Gibco) to obtain polyclonal NK cell populations.

Pan2D mAb Titration with Cynomolgus NK Cells.

Cynomolgus NK cells (NK bulk day 16) were incubated with different amount of Pan2D mAb followed by PE-conjugated goat F(ab')2 fragments anti-mouse IgG (H+L) antibodies. The percentage of positive cells was determined with an isotypic control (purified mouse IgG1). Samples were done in duplicate. Mean fluorescence intensity=MFI.

TABLE 2

KIR2DL1 epitope mapping

← Second Ab →

| First Ab (below) | DF200 | | Pan2D | | EB6 | | 1-4 F1 | | 1-7 F9 | | 1-6 F1 | | 1-6 F5 | |
|---|---|---|---|---|---|---|---|---|---|---|---|---|---|---|
| DF200 | | | | 80% | | 90% | 490 | 92% | 480 | 27% | 540 | 15% | 400 | 15% |
| | | | | | | | 40 | | 350 | | 460 | | 340 | |
| Pan2D | | 90% | | | | 90% | 900 | 95% | 860 | 2% | 750 | 12% | 600 | 13% |
| | | | | | | | 50 | | 840 | | 660 | | 520 | |
| EB6 | | 60% | | 40% | 460 | 57% | 370 | 48% | 490 | 65% | 260 | 23% | | nd |
| | | | | | 200 | | 190 | | 170 | | 200 | | | |
| 1-4 F1 | | | | | | | | | | | | | | |
| 1-7 F9 | 600 | 10% | 545 | 2% | 460 | 60% | 360 | 95% | | | 330 | 9% | | nd |
| | 545 | | 534 | | 180 | | 16 | | | | 300 | | | |
| 1-6 F1 | 350 | 11% | 475 | 7% | 260 | 18% | 360 | 23% | 490 | 10% | | | | nd |
| | 310 | | 440 | | 320 | | 275 | | 440 | | | | | |
| 1-6 F5 | 350 | 17% | 475 | 7% | | nd | 360 | 17% | | nd | 290 | 40% | | |
| | 290 | | 440 | | | | 300 | | | | 170 | | | |

TABLE 3

KIR2DL3 epitope mapping

| First Ab (below) | DF200 | | Pan2D | | gl183 | | 1-4 F1 | | 1-7 F9 | | 1-6 F1 | | 1-6 F5 | |
|---|---|---|---|---|---|---|---|---|---|---|---|---|---|---|
| DF200 | | | 75% | | 20% | | 1270<br>320 | 75% | 520<br>200 | 62% | 550<br>460 | 16% | 440<br>420 | 4% |
| Pan2D | 95% | | | | 85% | | 2250<br>730 | 68% | 880<br>750 | 15% | 840<br>770 | 8% | 560<br>460 | 18% |
| gl183 | 8% | | 40% | | | | 1300<br>330 | 75% | 670<br>160 | 76% | 530<br>430 | 18% | nd | |
| 1-4 F1 | 1140<br>210 | 82% | 2400<br>890 | 63% | 1240<br>330 | 73% | | | 1050<br>140 | 87% | | | | |
| 1-7 F9 | 770<br>450 | 42% | 870<br>830 | 5% | 800<br>200 | 75% | 1000<br>270 | 63% | | | | | | |
| 1-6 F1 | 790<br>760 | 4% | 990<br>1090 | 0% | 620<br>570 | 8% | | | | | | | | |
| 1-6 F5 | 800<br>760 | 5% | 990<br>950 | 4% | nd | | | | | | | | | |

TABLE 4

KIR2DS1 epitope mapping

| First Ab (below) | DF200 | | Pan2D | | 1-4 F1 | | 1-7 F9 | |
|---|---|---|---|---|---|---|---|---|
| DF200 | | | 70% | | 660<br>80 | 87% | 975<br>825 | 15% |
| Pan2D | 100% | | | | 650<br>-8 | 100% | 920<br>500 | 45% * |
| 1-7 F9 | 900<br>1090 | 17% | 1350<br>1200 | 11% | 660<br>23 | 96% | | |

Example 8

Epitope-Mapping of DF200- and pan2D-Binding to KIR2DL1

Computer modelling of the extra-cellular domains of KIR2DL1, -2 and -3 (KIR2DL1-3), based on their published crystal-structures (Maenaka et al. (1999), Fan et al. (2001), Boyington et al. (2000)), predicted the involvement of amino acids R131[1] in the interaction between KIR2DL1 and the KIR2DL1-3-cross-reactive mouse monoclonal antibodies (mAb's) DF200 and pan2D. To verify this, fusion-proteins were prepared consisting of the complete extra-cellular domain of KIR2DL1 (amino acids H1-H224), either wild-type or point-mutated (e.g. R131W[2]), fused to human Fc (hFc). The material and methods used to produce and evaluate the various KIR2DL1-hFc fusion-proteins have been described (Winter and Long (2000)). In short, KIR2DL1(R131W)-hFc encoding cDNA-vectors were generated, by PCR-based mutagenesis (Quickchange II, Promega) of CL42-Ig, a published cDNA-vector for the production of wild-type KIR2DL1-hFc (Wagtmann et al. (1995)). KIR2DL1-hFc and KIR2DL1(R131W)-hFc were produced in COS7 cells and isolated from tissue-culture media, essentially as described (Wagtmann et al. (1995)). To test their correct folding, KIR2DL1-hFc and KIR2DL1 (R131W)-hFc were incubated with LCL721.221 cells that express either HLA-Cw3 (no KIR2DL1 ligand) or HLA-Cw4 (KIR2DL1 ligand), and the interaction between KIR-Fc fusion proteins and cells analysed by FACS, a standard technique for the study of protein-interactions at the cell-surface. An example of independent experiments is given in FIG. 11, panel A. As predicted from the literature, none of the KIR2DL1-hFc fusion proteins hound HLA-Cw3 expressing LCL721.221 cells. In contrast, both KIR2DL1-hFc and KIR2DL1(R131W)-hFc bound to HLA-Cw4 expressing LCL721.221 cells, thereby confirming their correct folding.

[1] Single-letter amino acid code
[2] Substitution or R for W at amino acid position 131 (from N-terminus) in KIR2DL1

The binding of KIR2DL1(R131W)-hFc and KIR2DL1-hFc to KIR-specific mAb's (DF200, pan2D, EB6 and GL183) was studied using ELISA, a standard technique to study protein-interactions. In short, KIR2DL1(R131W)-hFc and KIR2DL1-hFc were linked to 96-wells plates via goat anti-human antibodies, after which KIR-specific mAb's were added in various concentrations (0-1 µg/ml in PBS). The interactions between KIR2DL1-hFc variants and mAb's were visualised by spectrophotometry (450 nm), using peroxidase-coupled secondary antibodies specific for mouse antibodies to convert TMB substrate. An examples of independent experiments is given in FIG. 11, panel B. Whereas the KIR2DL2-3-specific mAb GL183 was not able to bind any of the KIR2DL1-hFc fusion proteins, the KIR2DL1-specific mAb EB6, DF200 and pan2D bound KIR2DL1-hFc variants in a dose-dependent fashion. The single point-mutation (R131W) affected the binding of DF200 and pan2D with a reduction in binding compared to wild type of ~10% at highest concentrations of mAb (1 µg/ml), confirming that R131 is part of the binding-site of DF200 and pan2D in extra-cellular domain 2 of KIR2DL1.

REFERENCES

Moretta, A., Bottino, C., Pende, D., Tripodi, G., Tambussi, G., Vial; O., Orengo, A., Barbaresi, M., Merli, A., Ciccone, E., and et al. (1990). Identification of four subsets of human CD3-CD16+ natural killer (NK) cells by the expression of clonally distributed functional surface molecules: correlation between subset assignment of NK clones and ability to mediate specific alloantigen recognition. J Exp Med 172, 1589-1598.

Moretta, A., Vitale, M., Bottino, C., Orengo, A. M., Morelli, L., Augugliaro, R., Barbaresi, M., Ciccone, E., and Moretta, L. (1993). P58 molecules as putative receptors for major histocompatibility complex (MHC) class I molecules in human natural killer (NK) cells. Anti-p58 antibodies reconstitute lysis of MHC class I-protected cells in NK clones displaying different specificities. J Exp Med 178, 597-604.

Pende, D., Parolini, S., Pessino, A., Sivori, S., Augugliaro, R., Morelli, L., Marcenaro, E., Accame, L., Malaspina, A., Biassoni, R., et al. (1999). Identification and molecular characterization of NKp30, a novel triggering receptor involved in natural cytotoxicity mediated by human natural killer cells. J Exp Med 190, 1505-1516.

Ruggeri, L., Capanni, M., Urbani, E., Perruccio, K., Shlomchik, W. D., Tosti, A., Posati, S., Rogaia, D., Frassoni, F., Aversa, F., et al. (2002). Effectiveness of donor natural killer cell alloreactivity in mismatched hematopoietic transplants. Science 295, 2097-2100.

Wagtmann N, Biassoni R, Cantoni C, Verdiani S, Malnati M S, Vitale M, Bottino C, Moretta L, Moretta A, Long E O. Molecular clones of the p58 NK cell receptor reveal immunoglobulin-related molecules with diversity in both the extra- and intracellular domains. Immunity. 1995 May; 2(5):439-49.

Biassoni R, Verdiani S, Cambiaggi A, Romeo P H, Ferrini S, Moretta L. Human CD3-CD16+ natural killer cells express the hGATA-3 T cell transcription factor and an unrearranged 2.3-kb TcR delta transcript. Eur J Immunol. 1993 May; 23(5):1083-7.

Saulquin X, Gastinel L N, Vivier E. Crystal structure of the human natural killer cell activating receptor KIR2DS2 (CD158j) J Exp Med. 2003 Apr. 7; 197(7):933-8.

Gauthier, L., Lemmers, B., Guelpa-Fonlupt, V., Fougereau, M., and Schiff, C. µ-SLC physico-chemical interactions of the human preB cell receptor: implications for VH repertoire selection and cell signaling at the preB cell stage. Journal of Immunology, 162, 41-50. (1999).

Saunal, H. and Van Regenmortel, M. H. V., Mapping of viral conformation epitopes using biosensor measurements. Journal of Immunology, 183: 33-41 (1995).

Boyington J C; Motyka S A; Schuck P; Brooks A G; Sun P D. Nature, Vol. 405 (6786) pp. 537-543 (2000)

Fan Q R; Long E O; Wiley D C. Nature immunology, Vol. 2 (5) pp. 452-460 (2001)

Maenaka K; Juji T; Stuart D I; Jones E Y. Structure with Folding and design, Vol. 7 (4) pp. 391-398 (1999)

Wagtmann N; Rajagopalan S; Winter C C; Peruzzi M; Long E O. Immunity, Vol. 3 (6) pp. 801-809 (1995)

Winter C C; Long E O. Natural Killer Cells Protocols (edited by Campbell K S and Colonna M). Human Press. pp. 219-238 (2000)

All references, including publications, patent applications and patents, cited herein are hereby incorporated by reference to the same extent as if each reference were individually and specifically indicated to be incorporated by reference and were set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The invention claimed is:

1. A method of potentiating natural killer (NK) cell activity in a human patient in need thereof, comprising the step of administering to said human patient a monoclonal antibody or antigen-binding fragment thereof that binds at least two different human inhibitory Killer Immunoglobulin-Like Receptor (KIR) receptor gene products, wherein said monoclonal antibody or antigen-binding fragment thereof is capable of neutralizing KIR-mediated inhibition of NK cell cytotoxicity in NK cells expressing at least one of said two different human inhibitory KIR receptors, said monoclonal antibody or antigen-binding fragment thereof being present in an amount effective to detectably potentiate NK cell cytotoxicity in the human patient;

wherein said monoclonal antibody or fragment thereof is selected from the following:
- a) the DF200 antibody produced by the hybridoma DF200, deposited as CNCM I-3224, or an Fab, F(ab')$_2$, or scFv fragment thereof;
- b) a chimeric antibody comprising the complementarity determining regions (CDRs) of the DF200 antibody or an Fab, F(ab')$_2$, or scFv fragment thereof; or
- c) a humanized antibody or antigen-binding fragment thereof comprising the CDRs of the DF200 antibody.

2. The method of claim 1, wherein said monoclonal antibody is the DF200 antibody produced by the hybridoma DF200, deposited as CNCM I-3224.

3. The method of claim 1, wherein said antigen-binding fragment is an Fab, F(ab')$_2$, or scFv fragment of the DF200 antibody.

4. The method of claim 1, wherein said monoclonal antibody or antigen-binding fragment thereof is a chimeric antibody according to b) and further wherein said chimeric antibody comprises the entire variable regions of the DF200 antibody.

5. The method of claim 4, wherein said antigen-binding fragment is an Fab, F(ab')$_2$, or scFv fragment of said chimeric antibody.

6. The method of claim 1, wherein said monoclonal antibody or antigen-binding fragment thereof is a humanized antibody or antigen-binding fragment thereof according to c) comprising the CDRs of the DF200 antibody.

7. The method of claim 6, wherein said antigen-binding fragment is an Fab, F(ab')$_2$, or scFv fragment of said humanized antibody.

8. The method of claim 1, wherein said monoclonal antibody or antigen-binding fragment thereof binds to KIR2DL1 and KIR2DL2/3.

9. A method of potentiating natural killer (NK) cell activity in a human patient in need thereof, comprising the step of administering to said human patient an effective amount of a human, humanized or chimeric monoclonal antibody or antigen-binding fragment thereof that binds to Killer Immunoglobulin-Like Receptors (KIRs) KIR2DL1 and KIR2DL2/3, and further wherein said human, humanized or chimeric monoclonal antibody or antigen-binding fragment thereof inhibits binding of HLA-C molecules to KIR2DL1 and KIR2DL2/3 and, thus, is capable of neutralizing or inhibiting KIR-mediated inhibition of cell cytotoxicity by NK cells expressing any of the following (i) KIR2DL1, (ii) KIR2DL2/3, and (iii) a combination of KIR2DL1 and KIR2DL2/3;

wherein said monoclonal antibody or fragment thereof is a chimeric or humanized antibody or antigen-binding fragment thereof comprising the CDRs of the DF200 antibody deposited as CNCM I-3224, and wherein said human patient is suffering from cancer or an infectious disease.

10. A method of potentiating natural killer (NK) cell activity in a human patient in need thereof, comprising the step of administering to said human patient an effective amount of the DF200 antibody produced by the hybridoma DF200, deposited as CNCM I-3224, wherein said human patient is suffering from cancer or an infectious disease.

11. The method according to claim 9, which promotes lysis of matched or HLA compatible target cells by NK cells expressing KIR2DL1, KIR2DL2/3 or a combination thereof, wherein the target cells are not effectively lysed in the absence of the human, humanized or chimeric monoclonal antibody or antigen-binding fragment thereof.

12. The method of claim 11, wherein the NK cells in the absence of the human, humanized or chimeric monoclonal antibody or antigen-binding fragment thereof bind to at least one HLA-C molecule selected from Cw1, Cw2, Cw3, Cw4, Cw5, Cw6, an HLA-C molecule having a lysine residue at position 80, Cw7, Cw8, and an HLA-C molecule having an asparagine residue at position 80, and said binding is inhibited by said human, humanized or chimeric monoclonal antibody or antigen-binding fragment thereof.

13. The method of claim 12, wherein the NK cells in the absence of the human, humanized or chimeric monoclonal antibody or antigen-binding fragment thereof bind to at least one HLA-C molecule selected from Cw1, Cw3, Cw7, Cw8, and an HLA-C molecule having an asparagine residue at position 80, and said binding is inhibited by said human, humanized or chimeric monoclonal antibody or antigen-binding fragment thereof.

14. The method of claim 12, wherein the NK cells in the absence of the human, humanized or chimeric monoclonal antibody or antigen-binding fragment thereof bind to at least one HLA-C molecule selected from Cw2, Cw4, Cw5, Cw6 and an HLA-C molecule having a lysine residue at position 80, and said binding is inhibited by said human, humanized or chimeric monoclonal antibody or antigen-binding fragment thereof.

15. The method of claim 12, wherein the NK cells in the absence of the human, humanized or chimeric monoclonal antibody or antigen-binding fragment thereof bind to at least one HLA-C molecule selected from Cw1, Cw3, Cw7, Cw8, and an HLA-C molecule having an asparagine residue at position 80, and said binding is inhibited by said human, humanized or chimeric monoclonal antibody or antigen-binding fragment thereof, and said NK cells further bind to, in the absence of the human, humanized or chimeric monoclonal antibody or antigen-binding fragment thereof, at least one HLA-C molecule selected from Cw2, Cw4, Cw5, Cw6 and an HLA-C molecule having a lysine residue at position 80, and said binding is inhibited by said human, humanized or chimeric monoclonal antibody or antigen-binding fragment thereof.

16. The method of claim 1, wherein said human patient is suffering from cancer.

17. The method of claim 9, wherein said human patient is suffering from cancer.

18. The method of claim 10, wherein said human patient is suffering from cancer.

19. The method of claim 1, wherein said human patient is suffering from an infectious disease.

20. The method of claim 9, wherein said human patient is suffering from an infectious disease.

* * * * *